United States Patent
Wood

(10) Patent No.: US 12,121,937 B2
(45) Date of Patent: Oct. 22, 2024

(54) SYSTEM AND METHOD FOR CLEANING DISKS

(71) Applicant: Robert Eugene Wood, Concord, MI (US)

(72) Inventor: Robert Eugene Wood, Concord, MI (US)

(73) Assignee: Robert Eugene Wood, Concord, MI (US)

(*) Notice: Subject to any disclaimer, the term of this patent is extended or adjusted under 35 U.S.C. 154(b) by 521 days.

(21) Appl. No.: 17/358,875

(22) Filed: Jun. 25, 2021

(65) Prior Publication Data
US 2021/0402442 A1 Dec. 30, 2021

Related U.S. Application Data

(60) Provisional application No. 63/044,663, filed on Jun. 26, 2020.

(51) Int. Cl.
| | |
|---|---|
| *B08B 1/12* | (2024.01) |
| *A61L 2/10* | (2006.01) |
| *B08B 3/04* | (2006.01) |

(52) U.S. Cl.
CPC ............ *B08B 1/12* (2024.01); *A61L 2/10* (2013.01); *B08B 3/041* (2013.01); *A61L 2202/11* (2013.01); *A61L 2202/17* (2013.01)

(58) Field of Classification Search
None
See application file for complete search history.

(56) References Cited

U.S. PATENT DOCUMENTS

| | | | | |
|---|---|---|---|---|
| 3,748,677 A | * | 7/1973 | Frank ................ | H01L 21/67028 451/210 |
| 3,970,471 A | * | 7/1976 | Bankes ............. | H01L 21/67092 134/80 |
| 7,694,873 B1 | * | 4/2010 | Jones ...................... | G07F 9/105 232/27 |
| 2008/0257388 A1 | * | 10/2008 | Purton ..................... | B08B 1/02 134/62 |

FOREIGN PATENT DOCUMENTS

| | | | | |
|---|---|---|---|---|
| CN | 1603016 A | * | 4/2005 | |
| GB | 1434637 A | * | 5/1976 | ............... B08B 1/02 |

OTHER PUBLICATIONS

Machine translation: CN 1603016; Wu, S. (Year: 2005).*

* cited by examiner

*Primary Examiner* — Natasha N Campbell
(74) *Attorney, Agent, or Firm* — Vivacqua Crane, PLLC

(57) ABSTRACT

A system and method for cleaning disks includes a cleaning disk rotatably supported by a structural frame, the rotatable cleaning disk defining a plurality of holes, the plurality of holes carrying disks to be cleaned. The rotatable cleaning disk disposed between a first plurality of brushes and a second plurality of such that each of the first plurality of brushes and the second plurality of brushes contacting and agitating surfaces of the disks. A washing tank is supported by the structural frame and defines a reservoir of cleaning solution. At least a portion of the rotatable cleaning disk and the first and second pluralities of brushes are submerged in the cleaning solution. A blower forces heated air over the disks to be cleaned and removes cleaning solution from the disks, and a light source irradiates the disks to be cleaned for a predetermined amount of time.

10 Claims, 11 Drawing Sheets

SYSTEM AND METHOD FOR CLEANING DISKS

CROSS-REFERENCE TO RELATED APPLICATIONS

The present application claims priority to U.S. Provisional Patent Application Ser. No. 63/044,663 filed Jun. 26, 2020 and entitled "System and Method for Cleaning Disks," which is incorporated by reference herein in its entirety.

INTRODUCTION

The present disclosure relates to systems and methods for cleaning objects handled by large numbers of people. More specifically, the present disclosure relates to cleaning and sanitization devices and methods for chips such as poker chips in circulation at casinos and the like.

Cash value chips, token chips, and the like are used in a wide variety of applications from at-home game-play to small and large casino operations, as well as at arcades and other such venues. These chips can remain in circulation for extended periods of time. During these periods, the chips may be handled by any number of customers or players, as well as staff members. Generally, each person who handles the chips imparts or deposits some material on the chips, thereby increasing a quantity of dirt, grime, biological material, and the like to the surface of the chip. The addition of this dirt, grime, and biological material can have a number of detrimental effects, from decreasing the mechanical efficiency of machines which accept the tokens or chips, to optically obscuring the value of the chips, to increasing the potential for transmission of disease from person to person.

Accordingly, some larger-scale users of chips and tokens may occasionally attempt to clean the chips or tokens by using cleaning solutions, ultrasonic cleaning systems, and/or mechanical cleaning devices, such as brushes. However, typical chip or token cleaning devices require substantial human interaction to load and secure the chips or tokens in a chip or token holder or rack, manually applying a cleaning solution or series of such solutions, and in many cases manual agitation of the cleaning solution on the chips or tokens is required as well.

Accordingly, while current chip and or token cleaning systems and methods achieve their intended purpose, there is a need for a new system and method for cleaning and sanitizing chips, tokens, and other such objects that are regularly handled by multiple people, and which offers continuous cleaning capabilities with minimal human interaction, a high rate of throughput, and plug-and-play usability and portability.

SUMMARY

A system and method for cleaning disks including a structural frame supporting a rotatable cleaning disk, stationary disk housings with a plurality of brushes, a blower, a light, and a reservoir containing a cleaning solution are provided.

In several aspects of the present disclosure a system for cleaning disks includes a rotatable cleaning disk rotatably supported by a structural frame. The rotatable cleaning disk defines a plurality of holes. The plurality of holes carry disks to be cleaned. The rotatable cleaning disk is disposed between a first plurality of brushes and a second plurality of brushes. The first plurality of brushes faces the second plurality of brushes, each of the first plurality of brushes and the second plurality of brushes contacts and agitates surfaces of the disks. A washing tank is supported by the structural frame and defines a reservoir of cleaning solution. At least a portion of the rotatable cleaning disk is submerged in the cleaning solution in the washing tank. A blower is disposed opposite the washing tank and above the rotatable cleaning disk, the blower forcing air over the disks to be cleaned and removing cleaning solution from the disks. A light source is disposed proximate the blower and irradiates the disks to be cleaned for a predetermined amount of time.

In another aspect of the present disclosure the system further includes one or more enclosing panels extending across and affixed to the structural frame, the enclosing panels defining an enclosure within the structural frame.

In still another aspect of the present disclosure the system further includes a motor disposed within the enclosure and mounted to the structural frame, the motor having a shaft extending from a first end proximate the motor to a second end distal to the motor. A drive gear or pulley is mounted to and fixed for common rotation with the shaft of the motor proximate the second end of the shaft. A driven gear or pulley is mounted to and fixed for common rotation with a first end of a support shaft. The support shaft is rotatably mounted to the structural frame between the first end of the support shaft and a second end of the support shaft. The rotatable cleaning disk is mounted to and fixed for common rotation with the second end of the support shaft, the drive gear rotatably connected to the driven gear by a continuous drive belt.

In yet another aspect of the present disclosure the system further includes an inner disk housing supported by the structural frame, the first plurality of brushes mounted to the inner disk housing. An outer disk housing is parallel to the inner disk housing, the outer disk housing supported by the structural frame, the second plurality of brushes mounted to the outer disk housing. A cleaning disk is disposed between the inner disk housing and the outer disk housing. The first and second pluralities of brushes are separated by a distance less than a thickness of the cleaning disk and less than a thickness of the disks to be cleaned such that the first plurality of brushes contacts an inner surface of the cleaning disk and the second plurality of brushes contacts an outer surface of the cleaning disk. The cleaning disk is rotatably supported by the structural frame and rotated by the motor.

In still another aspect of the present disclosure the system further includes a plurality of holes formed through the cleaning disk. The holes disposed circumferentially around the cleaning disk and spaced apart from one another, the cleaning disk rotating at a predetermined rotational speed and positioned so that each of the plurality of holes is directly adjacent a feed mechanism at a single point in the rotation of the cleaning disk.

In yet another aspect of the present disclosure the feed mechanism is supported by the structural frame and automatically feeds disks to be cleaned into the system.

In still another aspect of the present disclosure the at least some of the first and second pluralities of brushes are submerged in the cleaning solution, the first and second pluralities of brushes agitating surfaces of the disks to be cleaned.

In yet another aspect of the present disclosure the blower forces air through an air guide, a portion of the cleaning disk passing through the air guide where air from the blower is forced over and dries the surfaces of the disks to be cleaned. A heating element is disposed proximate the blower and increasing a temperature of air flowing over the cleaning disks to between about 120° Fahrenheit and about 170° Fahrenheit.

In still another aspect of the present disclosure the light source is disposed in and supported by the air guide, light from the light source being incident upon the disks to be cleaned for at least fourteen seconds.

In yet another aspect of the present disclosure the irradiation device is a light source such as a ultraviolet (UV°) light source having at least a 20 watt capacity.

In still another aspect of the present disclosure an ejection port is formed through the inner disk housing and sized to allow passage of cleaned disks. An ejection tab is located at the ejection port and directs the cleaned disks through the ejection port and into a chute, the cleaned disks passing down the chute. A sorting tray is disposed at an end of the chute opposite the ejection tab and receives the cleaned disks from the chute.

In yet another aspect of the present disclosure a method for cleaning disks includes placing disks to be cleaned into a disk cleaning system. The disk cleaning system has a structural frame, a rotatable cleaning disk rotatably mounted to the structural frame and disposed between a first plurality of brushes and a second plurality of brushes. The first plurality of brushes located directly across from and facing the second plurality of brushes. The method further includes contacting and agitating surfaces of the disks to be cleaned with the first plurality of brushes and the second plurality of brushes. The method further includes rotating the rotatable cleaning disk at a predetermined rate, and submerging a portion of the rotatable cleaning disk, carrying the disks to be cleaned, in a washing tank for a predetermined quantity of time. The washing tank is mounted to the structural frame and defines a reservoir filled with a cleaning solution. The method further includes drying the disks to be cleaned by blowing a quantity of heated air over a portion of the rotatable cleaning disk that is not submerged in the washing tank, and irradiating the disks to be cleaned for a predetermined quantity of time. The method further includes ejecting cleaned disks from the disk cleaning system into a sorting tray.

In still another aspect of the present disclosure placing disks to be cleaned into a cleaning system further includes loading the disks to be cleaned into a feed mechanism supported by the structural frame and automatically feeding disks to be cleaned into the system. A plurality of holes is formed through the cleaning disk. The holes are disposed circumferentially around the cleaning disk and spaced apart from one another. The cleaning disk rotates at a predetermined rotational speed and is positioned so that each of the plurality of holes is directly adjacent the feed mechanism at a single point in the rotation of the cleaning disk.

In yet another aspect of the present disclosure agitating surfaces of the disks to be cleaned further includes passing the disks to be cleaned between the first plurality of brushes and the second plurality of brushes. The first plurality of brushes and the second plurality of brushes are separated by a distance less than a thickness of the cleaning disk and less than a thickness of the disks to be cleaned.

In still another aspect of the present disclosure rotating the rotatable cleaning disk at a predetermined rate further includes utilizing a motor mounted to the structural frame to rotate the cleaning disk via a drive gear or pulley mounted to and fixed for common rotation with a shaft of the motor and rotatably connected by a continuous drive belt to a driven gear or pulley. The driven gear or pulley is mounted to and fixed for common rotation with a first end of a support shaft. The support shaft is rotatably mounted to the structural frame between the first end of the support shaft and a second end of the support shaft. The rotatable cleaning disk is mounted to and fixed for common rotation with the second end of the support shaft. The motor through the continuous drive belt and the drive gear or pulley and the driven gear or pulley causes the rotatable cleaning disk to rotate at approximately 2.5 revolutions per minute.

In yet another aspect of the present disclosure drying the disks to be cleaned further includes utilizing blower supported by the structural frame opposite the washing tank, the blower forcing air through an air guide, a portion of the cleaning disk passing through the air guide where air from the blower is forced over and dries the surfaces of the disks to be cleaned. The method further includes heating the air in the air guide with a heating element disposed proximate the blower. The heating element increases a temperature of air flowing over the disks to be cleaned to between about 120° Fahrenheit and 170° Fahrenheit.

In still another aspect of the present disclosure heating the air in the air guide further includes increasing a temperature of air flowing over the disks to be cleaned to between about 130° Fahrenheit and 160° Fahrenheit.

In yet another aspect of the present disclosure heating the air in the air guide further includes increasing a temperature of air flowing over the disks to be cleaned to between about 145° Fahrenheit and about 155° Fahrenheit.

In still another aspect of the present disclosure irradiating the disks to be cleaned for a predetermined quantity of time further includes utilizing an ultraviolet (UV°) light source having at least a 20 watt capacity is disposed proximate the blower and irradiates the disks to be cleaned for at least fourteen seconds.

In yet another aspect of the present disclosure a system for cleaning disks includes a structural frame, and one or more enclosing panels extending across and affixed to the structural frame, the enclosing panels further defining an enclosure. A feed mechanism is supported by the structural frame and automatically feeding disks to be cleaned into the system. An inner disk housing is supported by the structural frame and has a first plurality of brushes. An outer disk housing is parallel to the inner disk housing. The outer disk housing is supported by the structural frame and has a second plurality of brushes placed directly opposite the first plurality of brushes so that the first plurality of brushes faces the second plurality of brushes. A cleaning disk is disposed between the inner disk housing and the outer disk housing such that the first plurality of brushes contacts an inner surface of the cleaning disk and the second plurality of brushes contacts an outer surface of the cleaning disk. The cleaning disk is rotatably supported by the structural frame and rotated by a motor. The motor is disposed within the enclosure and mounted to the structural frame. The motor has a shaft. A drive gear or pulley is mounted to and fixed for common rotation with the shaft of the motor. A driven gear or pulley is mounted to and fixed for common rotation with a first end of a support shaft. The support shaft is mounted to the structural frame between the first end of the support shaft and a second end of the support shaft. The cleaning disk is mounted to and fixed for common rotation with the second end of the support shaft. The drive gear is rotatably connected to the driven gear by a continuous drive belt. A plurality of holes is formed through the cleaning disk, the holes disposed circumferentially around the cleaning disk and spaced apart from one another. The cleaning disk is rotating at a predetermined rotational speed and positioned so that each of the plurality of holes is directly adjacent the feed mechanism at a single point in the rotation of the cleaning disk. A washing tank is supported by the structural frame and defines a reservoir of cleaning solution. The cleaning disk is positioned so that a portion of the cleaning disk is submerged into the cleaning solution, at least some of the first and second pluralities of brushes are submerged in the cleaning solution. The first and second pluralities of brushes are separated by a distance less than a thickness of the cleaning disk and less than a thickness of the disks to be cleaned. The first and second pluralities of brushes contacting and agitating surfaces of the disks to be cleaned. A blower is supported by the structural frame opposite the washing tank. The blower forces air through an air guide. A portion of the cleaning disk passes through the air guide where air from the blower is forced over and dries the surfaces of the disks to be cleaned. An irradiation device is disposed in and supported by the air guide. Light from the irradiation device is incident upon the disks to be cleaned for a predetermined period of time. An ejection is port formed through the inner disk housing and sized to allow passage of disks which have now been cleaned. An ejection tab is located at the ejection port and forces cleaned disks through the ejection port and into a chute. Cleaned disks pass down the chute into a sorting tray disposed at an end of the chute opposite the ejection tab. The sorting tray receives cleaned disks from the chute.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
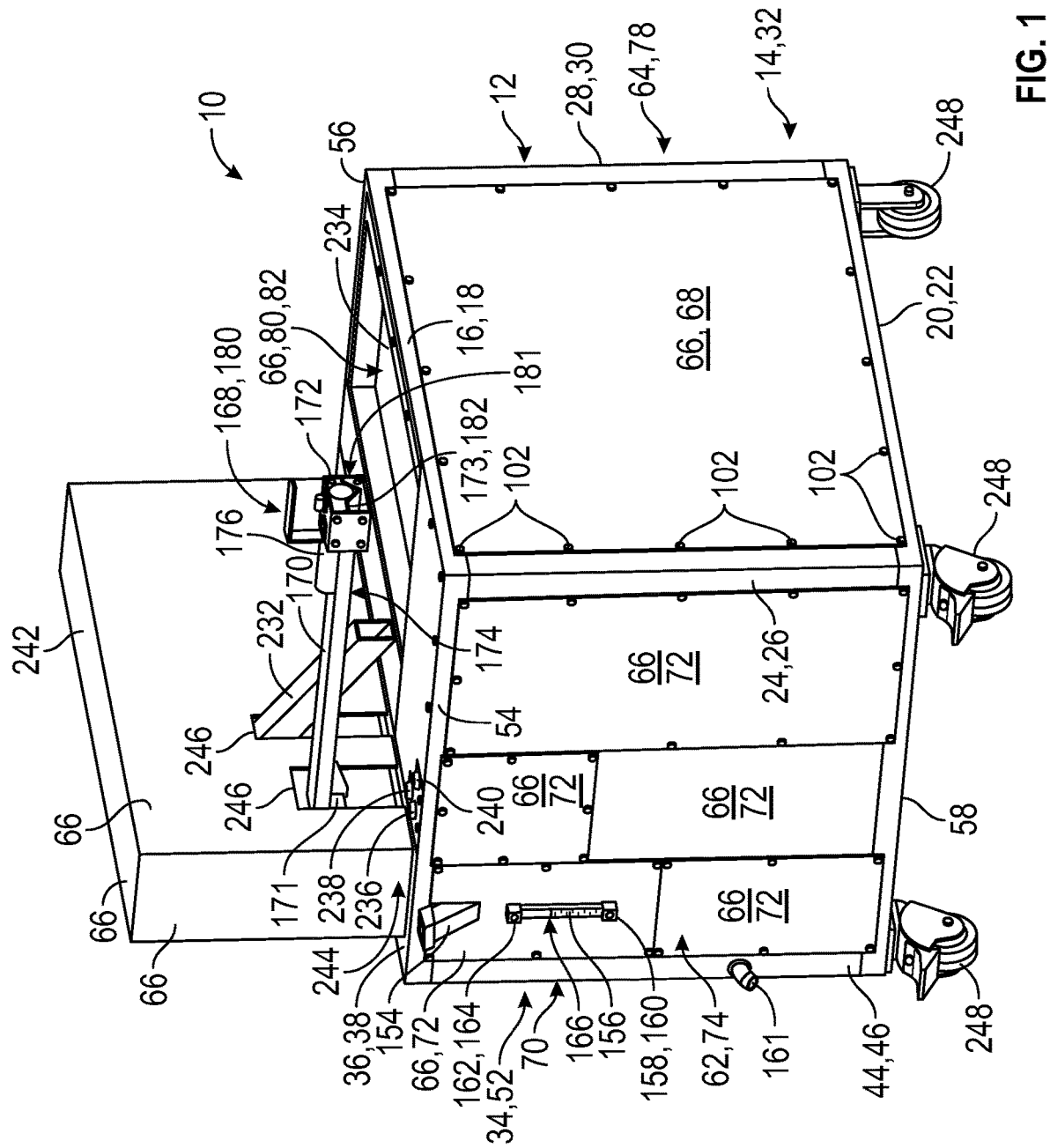
FIG. 1 is a perspective front view of a system and method for cleaning disks according to an exemplary embodiment.

Referring to FIG. 1, a perspective environmental view of a system 10 for cleaning disks is shown. For the sake of simplicity and ease of understanding, the system 10 will be described herein as a system 10 that operates to clean and sanitize poker chips. However, it should be appreciated that the system 10 could easily be adapted to clean other objects such as tokens, coins, and the like, as well as other disc-shaped objects like hockey pucks, frisbees, plates, and the like. Likewise, with minor modifications, the components of the system 10 which will be described in detail below may be adapted to clean non disc-shaped objects without departing from the scope or intent of the present disclosure. Accordingly, the fact that the bulk of this detailed description will focus on a poker chip cleaning system 10 and method should be regarded as a non-limiting example of the technology disclosed herein.

The system 10 has a structural frame 12. The structural frame 12 may be formed of any of a variety of different components including but not limited to: round, square, or angled-section bars, brackets, and the like. In further non-limiting examples, the components forming the structural frame 12 may be formed of metals, metal alloys, plastics, composite materials, or the like. As shown in the figures, the structural frame 12 defines at least the edges of a rectangular prism shape, however, it should be appreciated that depending on a variety of factors, the overall shape of the structural frame 12 may vary substantially from the rectangular prism described herein. Such factors include, but are not limited to: physical packaging needs of the system 10, spatial constraints for a location in which the system 10 is to be used, variations in size and shape of the a variety of system 10 components which will be described further herein, and the like. The structural frame 12 may be composed of a plurality of individual frame components, a plurality of sub-frames, or the like.

In a non-limiting example of a rectangular prism-shaped structural frame 12, at a front 14 of the structural frame 12, a front top bar 16 defines a top front edge 18 of the structural frame 12. A front bottom bar 20 disposed substantially directly below and parallel to the front top bar 16 defines a bottom front edge 22 of the structural frame 12. A left front side bar 24 extends substantially perpendicularly from the front bottom bar 20 to the front top bar 16 at a left front edge 26 of the front 14 of the structural frame 12. The left front side bar 24 is substantially vertical and the front top and bottom bars 16, 20 are substantially horizontal. A right front side bar 28 extends substantially perpendicularly from the front bottom bar 20 to the front top bar 16 at a right front edge 30 of the front 14 of the structural frame 12. The left and right front side bars 24, 28 are substantially parallel to each other. In some aspects, the front top bar 16, front bottom bar 20, left front side bar 24, and right front side bar 28 may be assembled or otherwise formed together to form a front sub-frame 32.

At a rear 34 of the structural frame 12, a rear top bar 36 defines a top rear edge 38 of the structural frame 12. A rear bottom bar 40 is disposed substantially directly below and parallel to the rear top bar 36 and defines a bottom rear edge 42 of the structural frame 12. A left rear side bar 44 extends substantially perpendicularly from the rear bottom bar 40 to the rear top bar 36 at a left rear edge 46 of the rear 34 of the structural frame 12. The left rear side bar 44 is substantially vertical and the rear top and bottom bars 36, 40 are substantially horizontal. A right rear side bar 48 extends substantially perpendicularly from the rear bottom bar 38 to the rear top bar 36 at a right rear edge 50 of the rear 34 of the structural frame 12. The left and right rear side bars 44, 48 are substantially parallel to each other. In some aspects, the rear top bar 36, rear bottom bar 40, left rear side bar 44, and right rear side bar 48 may be assembled or otherwise formed together to form a rear sub-frame 52.

When assembled together, each of the front and rear sub-frames 32, 52 are substantially planar and parallel to one another. The front and rear sub-frames 32, 52 are affixed to one another by a plurality of structural members extending perpendicularly from the front sub-frame 32 to the rear sub-frame 52. For example, a top left connector 54 extends from the junction of the front top bar 16 and the left front side bar 24 to the junction of the rear top bar 36 and the left rear side bar 44. Likewise, a top right connector 56 extends from the junction of the front top bar 16 and the right front side bar 28 to the junction of the rear top bar 36 and the right rear side bar 48. The top left and top right connectors 54, 56 are substantially parallel to one another and perpendicular to the substantially planar front and rear sub-frames 32, 52. Similarly, a bottom left connector 58 extends from the junction of the front bottom bar 20 and the left front side bar 24, to the junction of the rear bottom bar 40 and the left rear side bar 44. A bottom right connector 60 extends from the junction of the front bottom bar 20 and the right front side bar 28 to the junction of the rear bottom bar 40 and the right rear side bar 48. The bottom left and right connectors 58, 60 are parallel to one another, and parallel to the top left and right connectors 54, 56. In some examples, top and bottom left connectors 54, 58 and the front and rear left side bars 24, 44 may form a left sub-frame 62, and the top and bottom right connectors 56, 60 and the front and rear right side bars 28, 48 may form a right sub-frame 64, where the left and right sub-frames 62, 64 are attached to one another by the front and rear top and bottom bars 16, 20, 36, 40.

A plurality of enclosing panels 66 extend across the structural frame 12, thereby enclosing the substantially rectangular-prism shaped structural frame 12. A front panel 68 extends from the front left side bar 24 to the right front side bar 28 and from the front top bar 16 and the front bottom bar 20. A rear panel 70 extends from the rear left side bar 44 to the rear right side bar 48 and from the rear top bar 36 to the rear bottom bar 40. In some examples, the front and rear panels 68, 70 are formed of a single sheet of material, such as sheet metal, plastic, composite, or other such materials. In other examples, the front and rear panels 68, 70 may be formed of a plurality of sub-panels sized and shaped to provide easy access to componentry within or enclosed by the structural frame 12 and the front and rear panels 68, 70.

A plurality of left side panels 72 extend from the front left side bar 24 to the left rear side bar 44 and from the left top connector 54 to the bottom left connector 58 and enclose a left side 74 of the structural frame 12. Likewise, at least one right side panel 76 extends from the front right side bar 28 to the right rear side bar 48 and from the top right connector 56 to the bottom right connector 60, thereby enclosing a right side 78 of the structural frame 12.

One or more top panels 80 define a top surface 82 of the system 10. The top panels 80 extend substantially from the top left connector 54 to the top right connector 56 and from the front top bar 16 towards the rear top bar 36. One or more bottom panels 84 define a bottom surface 86 of the system 10. The bottom panels 84 extend substantially from the bottom left connector 58 to the bottom right connector 60 and from the front bottom bar 20 to the rear bottom bar 40.

In several aspects, each of the plurality of enclosing panels 66, including, but not limited to the left side panels 72, right side panel 76, the top panels 80, and the bottom panels 84 is bonded or otherwise attached to the structural frame 12 by mechanical, thermal, or chemical fastening means, such as screws, bolts, nuts, rivets, interference connections, glues or other adhesives, welds, braised joints, or the like. The fastening means may vary from panel to panel, or from location to location around the structural frame 12 of the system 10. In some examples, one or more of the plurality of panels 66 is removable to gain access to components within the enclosure 88 defined by the structural frame 12.

Figure 2:
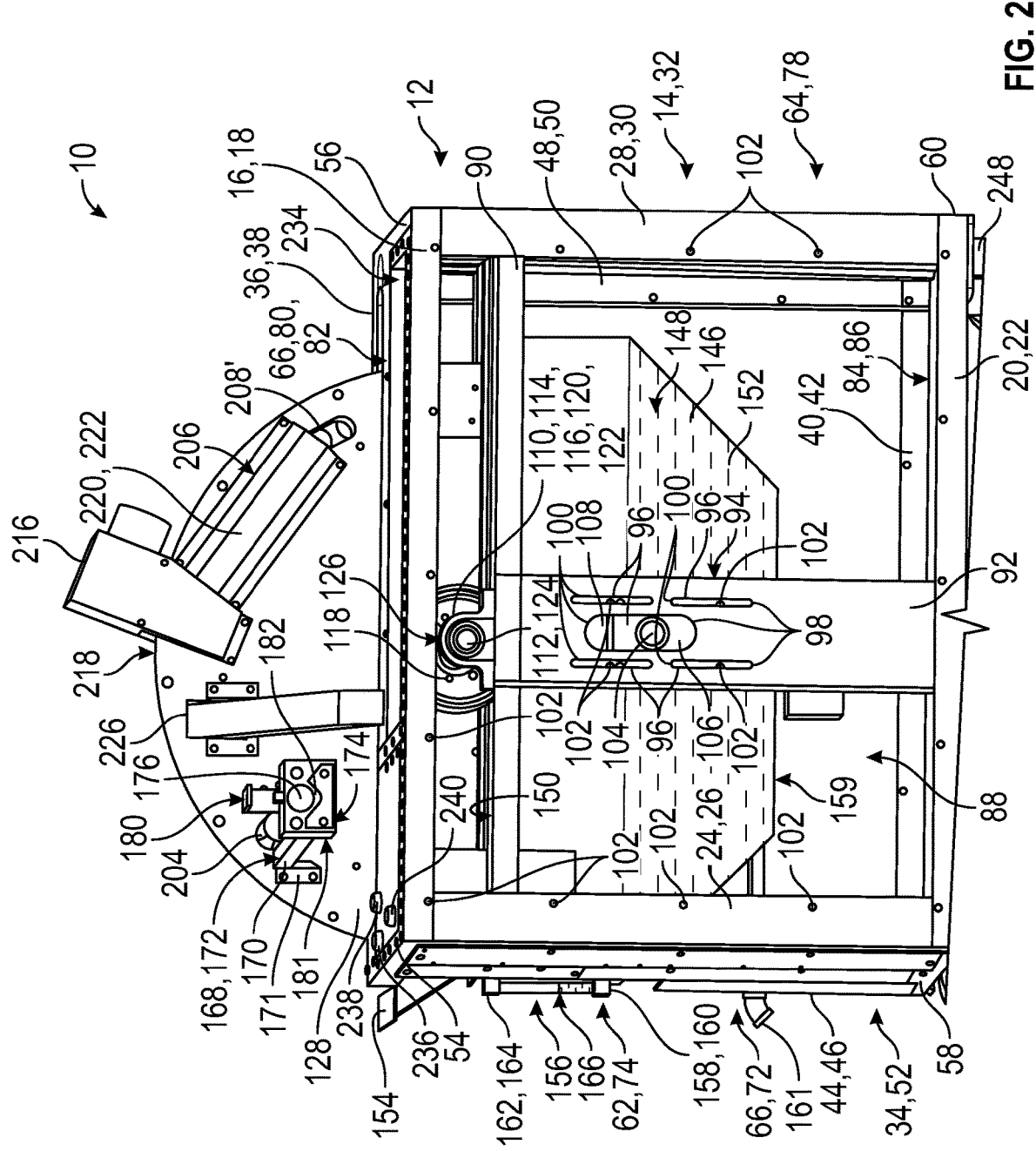
FIG. 2 is a partial perspective front view of the system and method for cleaning disks of FIG. 1 in which a front, side, and rear panel have been removed to show an internal aspect of the system and method of FIG. 1 according to an exemplary embodiment.

Turning now to FIG. 2, and with continuing reference to FIG. 1, a front perspective view of a portion of the system 10 is shown with the front and rear panels 68, 70 removed. A horizontal brace 90 extends substantially from the left side 74 to a right side 78 of the structural frame 12. The horizontal brace 90 increases lateral rigidity of the structural frame 12 relative to a version of the structural frame 12 without the horizontal brace 90. A vertical brace 92 extends substantially from the bottom panel or panels 84 to the horizontal brace 90. The vertical brace 92 is substantially perpendicular to the horizontal brace 90 and the bottom panel or panels 84. The horizontal brace 90 and the vertical brace 92 are attached or affixed to the structural frame 12 by mechanical, thermal, or chemical fastening means, as described above. In some examples one or more brackets or braces (not specifically shown) interconnect the horizontal brace 90, the vertical brace 92, and the structural frame 12. Similarly, the various components of the structural frame 12 may be interconnected by brackets or braces (not specifically shown).

A motor 94 is supported by one or more of the structural frame 12 and the horizontal and vertical braces 90, 92. The precise type of motor 94 may vary from application to application, but should be understood to be a device which provides rotational motion to one or more components of the system 10. In some examples, the motor 94 is an electromechanical device which converts electrical energy into mechanical energy. Furthermore, it should be appreciated that the motor 94 may take other forms and/or use non-electrical motivational means, such as hydraulic, pneumatic, or purely mechanical (for example spring-based) power to provide rotational or linear motion to one or more components of the system 10. More specifically, the motor 94 is mounted to the structural frame 12 by one or more attachment apertures or slots 96 formed in the structural frame 12. In some examples, the apertures or slots 96 are formed through the vertical brace 92 of the structural frame 12. When slots 96 are used, the slots 96 extend vertically from a lower end 98 to an upper end 100. One or more attachment features 102 extend from the motor 94 and into the apertures or slots 96 thereby secure the motor 94 to the structural frame 12. In several examples, the attachment features 102 may include threaded rods, studs, bolts, nuts, rivets, and the like, as well as interference connections, and the like. In further examples, the attachment features 102 may engage with secondary attachment features (not specifically shown) such as nuts, weld-nuts, threaded fittings, and the like, thereby securing the motor 94 to the structural frame 12.

A shaft 104 extends from the motor 94 horizontally to a drive gear or pulley 106 distal to the motor 94. In some examples, the drive gear or pulley 106 extends in a substantially vertical plane within a cavity 108 of the vertical brace 92. In other examples, the drive gear or pulley 106 extends in a substantially vertical plane and parallel to the vertical brace 92 of the structural frame 12. The drive gear or pulley 106 may take any of a variety of common toothed or un-toothed forms including but not limited to: spur gears, helical gears, and the like, or pulleys for engaging with flat, toothed, v-belt, round, or other such drive belts 108. In some examples, a continuous drive belt 108 is engaged with the drive gear or pulley 106 and extends in a vertical plane parallel to the drive gear or pulley 106 to a driven gear or pulley 110. The driven gear or pulley 110 is rotatably mounted to the structural frame 12 via a support shaft 112. The support shaft 112 extends substantially horizontally from the structural frame 12 from a first end 114 which is rotatably supported on the structural frame 12 by a bearing 116, to a second end 118 distal to the first end 114.

In some examples, the driven gear or pulley 110 is mounted to the vertical brace 92 via the support shaft 112 at a location above, relative to the drive gear or pulley 106, and proximate the first end 114 of the support shaft 112. The bearing 116 may be a single bearing, or a plurality of bearings without departing from the scope or intent of the present disclosure. The bearing 116 may be any form of bearing including, but not limited to: needle bearings, roller bearings, ball bearings, thrust bearings, or the like. In some examples, an outer race 120 of the bearing 116 is affixed to the structural frame 12 by a bracket 122. The bracket 122 is sized and shaped to receive and immovably secure the outer race 120 of the bearing 116 relative to both the bracket 122 and the structural frame 12. However, an inner race 124 of the bearing 116 is free to rotate relative to the outer race 120. More specifically, the inner race 124 of the bearing 116 is affixed for common rotation with the support shaft 112. Likewise, the support shaft 112 is fixed for common rotation with the driven gear or pulley 110 at the first end 114.

The second end 118 of the support shaft 112 extends through a first housing aperture 126 in an inner disk housing 128 and is fixed for common rotation with a cleaning disk 130. The inner disk housing 128 is supported by the structural frame 12. In some examples, the inner disk housing 128 is affixed to and supported by the horizontal and/or vertical braces 90, 92 via a plurality of attachment features (not specifically shown). The attachment features may be any one or a combination of mechanical, thermal, or chemical fastening means like screws, bolts, nuts, rivets, interference connections, glues or other adhesives, welds, braised joints, or the like.

In some examples, the motor 94 is a combined motor-gearbox assembly 94'. The combined motor-gearbox assembly 94' may include one or more internal gears or pulleys and belts driven by a motor 94 within a housing (not specifically shown). The combined motor-gearbox assembly 94' uses the one or more internal gears, pulleys, belts, and the like to adjust a rotational speed of the motor 94 to a desired rotational speed of the cleaning disk 130. In some examples, the combined motor-gearbox assembly 94' may include a plurality of gear ratios allowing the motor-gearbox assembly 94' to provide various predefined rotational speeds for the drive gear or pulley 106. In still further examples, the combined motor-gearbox assembly 94' may be a continuously variable transmission (CVT) capable of providing any of a wide range of rotational speeds for the drive gear or pulley 106.

The cleaning disk 130 is sandwiched between the inner disk housing 128 and an outer disk housing 132. Like the inner disk housing 128, the outer disk housing 132 is supported by the structural frame 12 via a plurality of attachment features (not specifically shown). The inner and outer disk housings 128, 132 are substantially congruent and each has an inner face 134', 134" which faces the cleaning disk 130. That is, the inner face 134' of the inner disk housing 128 faces an inner surface 136 of the cleaning disk 130, while the inner face 134" of the outer disk housing 132 faces an outer surface 138 of the cleaning disk 130. Each of the inner disk housing 128, cleaning disk 130, and outer disk housing 132 may be formed of any of a variety of materials, such as metals, metal alloys, composite materials, nylons, plastics, high-density polyethylene (HDPE), polytetrafluoroethylene (PTFE), or the like. In one example, each of the inner disk housing 128, cleaning disk 130, and outer disk housing 132 are formed of ultra high molecular weight polyethylene (UHMW) having predetermined friction and hardness characteristics. In several aspects, each of the inner disk housing 128, outer disk housing 132, and the cleaning disk 130 is substantially circular and have substantially similar diameters. In one example, the cleaning disk 130 has a diameter of between about 20 inches and about 54 inches. In another somewhat more compact example, the cleaning disk 130 has a diameter of between about 24 inches and about 40 inches. In a still more compact and portable example, the cleaning disk 130 has a diameter of between about 30 inches and about 36 inches. In one particular example, the cleaning disk 130 has a diameter of approximately 32 inches.

A plurality of brushes 140 are mounted circumferentially around the inner face 134' of the inner disk housing 128 and the inner face 134" of the outer disk housing 132. The quantity of brushes 140 on each of the inner faces 134', 134" may vary depending on the particular application without departing from the scope or intent of the present disclosure. In one example, at least twelve brushes 140 are mounted to the inner faces 134', 134" of each of the inner disk housing 128 and the outer disk housing 132. The brushes 140 on the inner face 134' of the inner disk housing 128 extend towards and contact the inner surface 136 of the cleaning disk, while the brushes 140 on the inner face 134" of the outer disk housing 132 extend towards and contact the outer surface 138 of the cleaning disk 130.

A plurality of circumferentially-arranged apertures or holes 142 are spaced around the perimeter 144 of the cleaning disk 130. Each of the holes 142 is sized and shaped to accept and loosely retain an object to be cleaned. In one example, the objects to be cleaned are substantially flat, disc-shaped objects such as cash value chips, token chips, poker chips, coins, plates, or the like. However, it should be appreciated that with minor adjustments in the shape and size of certain components described herein, the system 10 may be used to clean non disk shaped objects, such as cubes, spheres, rectangular plates or other planar reusable objects, or the like without departing from the scope or intent of the present disclosure. In the example, the holes 142 of the cleaning disk 130 are substantially circular openings formed through the entire thickness or depth of the cleaning disk 130, and sized somewhat larger than the diameter of the cash value chips, token chips, poker chips, coins, plates, or the like. The slight over-sizing of the holes 142 relative to the objects to be cleaned allows the objects to move around within the holes 142. While the holes 142 have been described as being substantially circular and designed for carrying substantially circular objects, it should be appreciated that other hole 142 shapes for carrying other objects may be used without departing from the scope or intent of the present disclosure. Accordingly, with minor adaptations, resizing of components, and the like, the technology described in this application may be used to clean objects which are not flat, and which may not be circular at all. Likewise, it should be appreciated that the quantity of brushes 140 may vary substantially, and may relate specifically to the size of the cleaning disk 130, and the quantity of holes 142 formed in the cleaning disk 130.

A washing tank 146 is suspended from the structural frame 12 of the system 10. The washing tank 146 is an open-topped reservoir for containing a cleaning solution 148. The washing tank 146 is suspended from the structural frame 12 by a plurality of attachment features (not specifically shown) which may include, but are not limited to: threaded rods, studs, bolts, nuts, rivets, and the like, as well as interference connections, retaining flanges, and the like. In further examples, the attachment features may engage with secondary attachment features (not specifically shown) such as nuts, weld-nuts, threaded fittings, and the like, thereby securing the washing tank 146 to the structural frame 12. In a particular example, the washing tank 146 is suspended from the structural frame 12 such that a top 150 of the washing tank 146 is attached to the horizontal brace 90. The cleaning disk 130 and the inner disk housing 128 and outer disk housing 132 are arranged so that a portion of each of the inner and outer disk housings 128, 132, and the cleaning disk 130 are within, but spaced apart from walls 152 of the washing tank 146. The washing tank 146 may be formed of any of a wide variety of materials, including, but not limited to metals, metal alloys, composite materials, nylons, plastics, high-density polyethylene (HDPE), polytetrafluoroethylene (PTFE), or the like. Accordingly, because the washing tank 146 is sized and shaped to accept and partially contain each of the inner and outer disk housings 128, 132, and the cleaning disk 130, the washing tank 146 has a somewhat semi-circular shape. However, for simplicity of manufacture and cost reduction, the tank may take the shape of an open-topped trapezoidal prism, a rectangular prism, a triangular prism or pyramidal prism, a semi-cylindrical trough or any other such shape without departing from the scope or intent of the present disclosure.

The cleaning solution 148 is provided to the washing tank 146 via a filler neck 154. The filler neck may be formed of any of a variety of known materials, and may extend from outside the system through at least one of the panels 66, such as one of the left side panels 72 to and through one or more of the walls 152 of the washing tank 146. The filler neck 154 provides a means of filling the washing tank 146 with cleaning solution 148 without having to remove one or more of the panels 66 to access the washing tank 146 directly. A sight glass 156 is also attached one or more of the panels 66 and provides a visible measure of a quantity of cleaning solution 148 within the washing tank 146. That is, the sight glass 156 has a feed tube 158 that extends to a known position 160 within the washing tank 146 and an outlet tube 162 that extends to an overflow position 164 in the washing tank 146 with a nominal tank level 166 disposed therebetween. The nominal tank level 166 is also displayed on the sight glass 156 so that a system user can ascertain the current quantity of cleaning solution 148 within the washing tank 146. A sump 157 is disposed at a bottom 159 of the washing tank 146 and includes a drain plug or pipe 161. The drain plug or pipe 161 may include a valve or stop cock (not specifically shown) which operates to allow an operator to selectively empty the contents of the washing tank 146.

Figure 3:
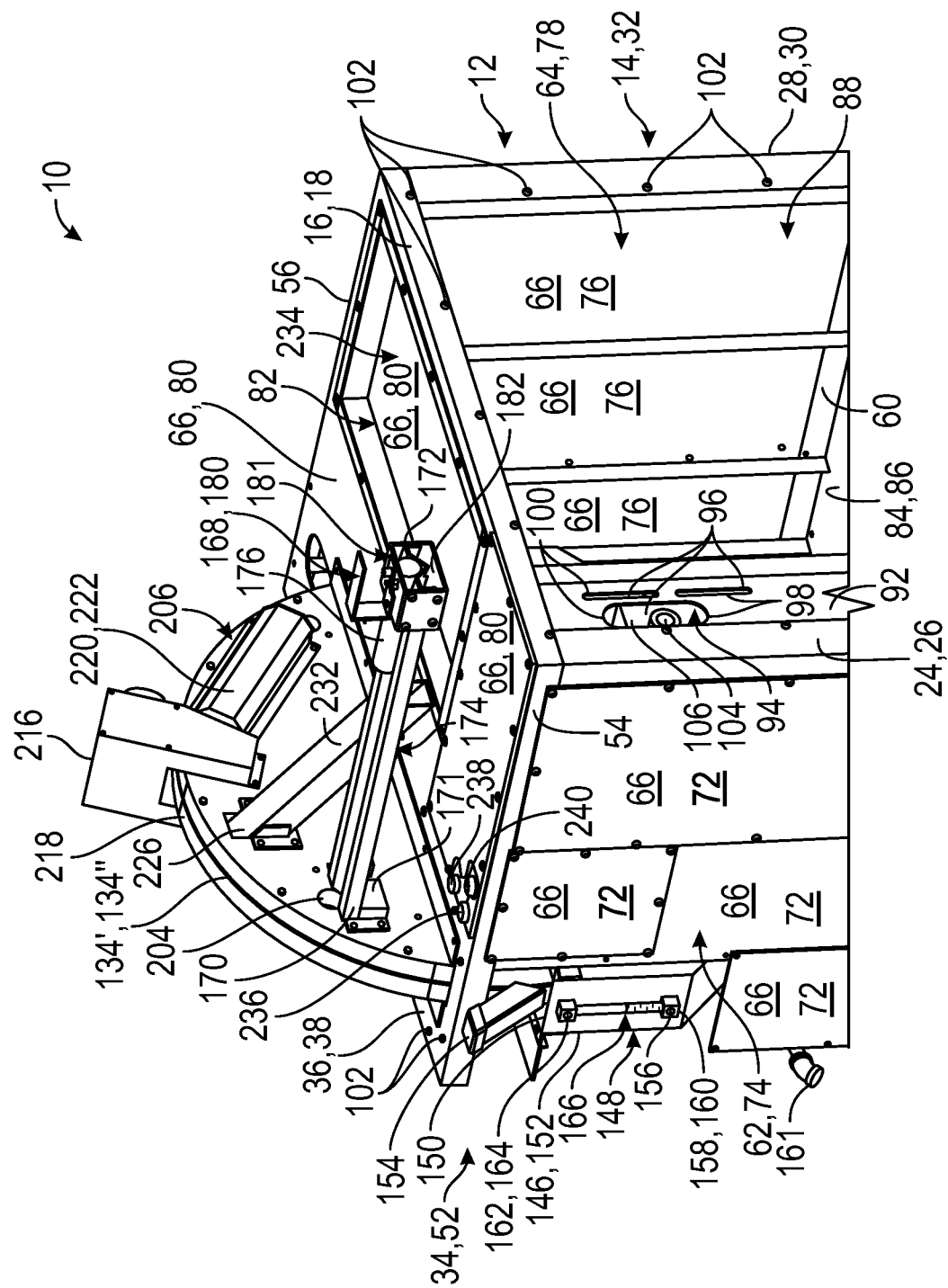
FIG. 3 is an enlarged partial perspective front view of the system and method for cleaning disks of FIG. 2 according to an exemplary embodiment.
Figure 4:
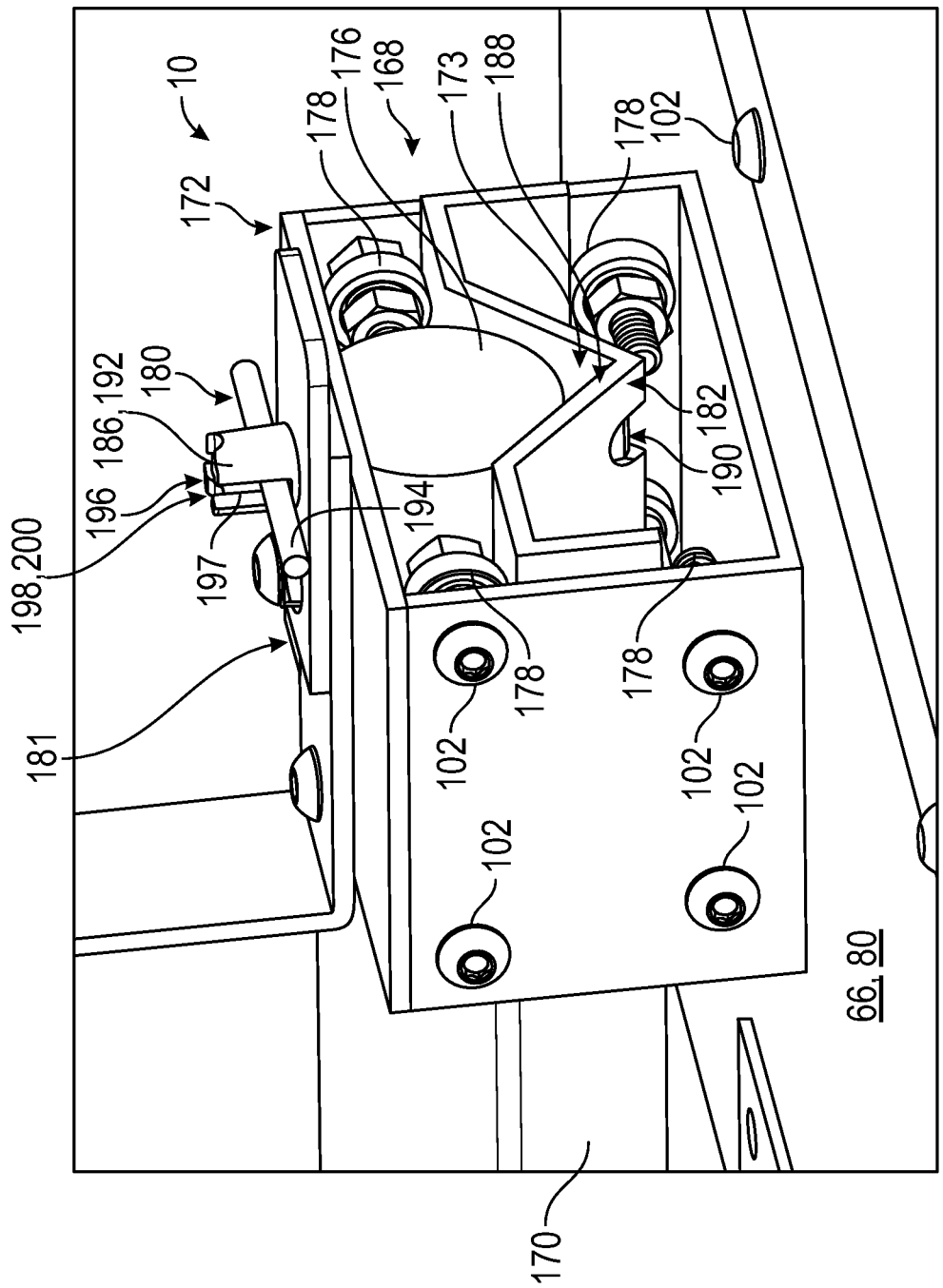
FIG. 4 is an enlarged perspective side view of a disk or chip loading mechanism of the system and method for cleaning disks according to an exemplary embodiment.

Turning now to FIGS. 3 and 4, and with continuing reference to FIGS. 1-2, a feed mechanism 168 automatically feeds objects to be cleaned into the system 10. The feed mechanism 168 is rigidly mounted to the system 10. In some examples, the feed mechanism 168 is mounted to the structural frame 12 of the system 10. In other examples, the feed mechanism 168 is mounted to the inner disk housing 128. In several aspects, the feed mechanism 168 is substantially horizontal and orthogonal to the plane defined by the cleaning disk 130. A plurality of attachment features 102 affix the feed mechanism 168 to the structural frame 12 and/or to the inner disk housing 128. In several examples, the attachment features 102 may include support flanges, threaded rods, studs, bolts, nuts, rivets, and the like, as well as interference connections, and the like. More specifically, a guide rail 170 of the feed mechanism 168 is attached to the structural frame 12 and/or the inner disk housing 128 of the system 10 at a distal end 171 by the attachment features 102.

In one example, the guide rail 170 for disc-shaped objects has a substantially V-shaped channel 173 in which a plurality of disc-shaped objects can be horizontally stacked, loaded, and supported. A trolley 172 moves the objects to be cleaned towards the cleaning disk 130. In several aspects, a spring 174 is attached to both the trolley 172 and to either or both of the guide rail 170 and the structural frame 12. The spring 174 is in tension and cause the trolley 172 to be biased towards the cleaning disk 130, thereby causing objects to be cleaned to be moved towards the cleaning disk 130. The trolley 172 further includes a horizontal pusher 176 that supports and maintains the objects to be cleaned within the guide rail 170. The horizontal pusher 176 can take any of a variety of different shapes including, but not limited to: rectangular prismatic shapes, octagonal prismatic shapes, horizontally-oriented cylindrical shapes, and the like. The trolley 172 is movably mounted to the guide rail 170 via one or more trolley bearings 178 or wheels. The trolley bearings 178 are rotatably affixed to the trolley 172 by one or more attachment features 102 such as bolts, nuts, rivnuts, studs, threaded rods, studs, rivets, and the like, as well as interference connections, and the like. The trolley bearings 178 are disposed on the trolley 172 in an orientation that allows the trolley 172 to move along the longitudinal axis 179 of the guide rail 170 but prevents the trolley 172 from moving laterally away from the axis 179 of the guide rail. The trolley bearings 178 may be any known form of bearings, including needle bearings, roller bearings, ball bearings, or the like. Additionally, the trolley bearings 178 may be formed of any of a variety of known materials, such as metals, metal alloys, ceramics, nylons, plastics, PTFEs, UHMWs, composite materials, rubbers and rubber compounds, or the like. Furthermore, it should be noted that while the trolley bearings 178 are shown in a substantially vertical orientation relative to the structural frame 12, the trolley bearings 178 may be mounted horizontally, or at any angle between vertical and horizontal which also provides for the trolley 172 to move smoothly along the guide rail 170. Likewise, in some examples, the trolley bearings 178 may be oriented in multiple planes, i.e. some in a vertical orientation, others in a horizontal orientation, or any angular orientation therebetween. The trolley bearings 178 rollably engage with the guide rail 170, thereby providing the trolley 172 with means to roll smoothly along the guide rail 170.

A spring-loaded release mechanism 180 selectively locks the trolley 172 in a locked position 181 at a proximal end 182 of the guide rail 170. The release mechanism 180 is biased by a second spring 184 in the locked position 181 in which the release mechanism 180 is biased downwards. The release mechanism 180 includes a piston 186 which slides vertically through an orifice 188 formed through the horizontal pusher 176 and locks the trolley 172 in the locked position 181 via a lock orifice 190 formed through the guide rail 170. The release mechanism 180 further includes a retainer 192 for a locking bar 194. The locking bar 194 is affixed to a top surface 196 of the piston 186. The locking bar 194 is rotatable relative to the trolley 172 and the guide rail 170. In the locked position 181, the locking bar 194 resides within a horizontal slot 197 formed in the retainer 192. The horizontal slot 197 extends a plane substantially parallel to the plane defined by the front 14 of the structural frame 12. When the locking bar 194 is lifted up and released from the horizontal slot 197 in the retainer 192, the trolley 172 is free to move along the guide rail 170. For ease of use, and so that human intervention is not constantly required, the locking bar 194 can be rotated to an unlocked position 198 and seated in a channel 200 formed in the top of the retainer 192. The channel 200 is substantially orthogonal to the horizontal slot 197 and extends for a depth substantially less than the horizontal slot 197. Accordingly, when the locking bar 194 is disposed in the channel 200, the piston 186 is held in the unlocked position 198 where the piston 186 is withdrawn from both the orifice 188 in the horizontal pusher 176 and the lock orifice 190 in the guide rail 170.

Figure 5:
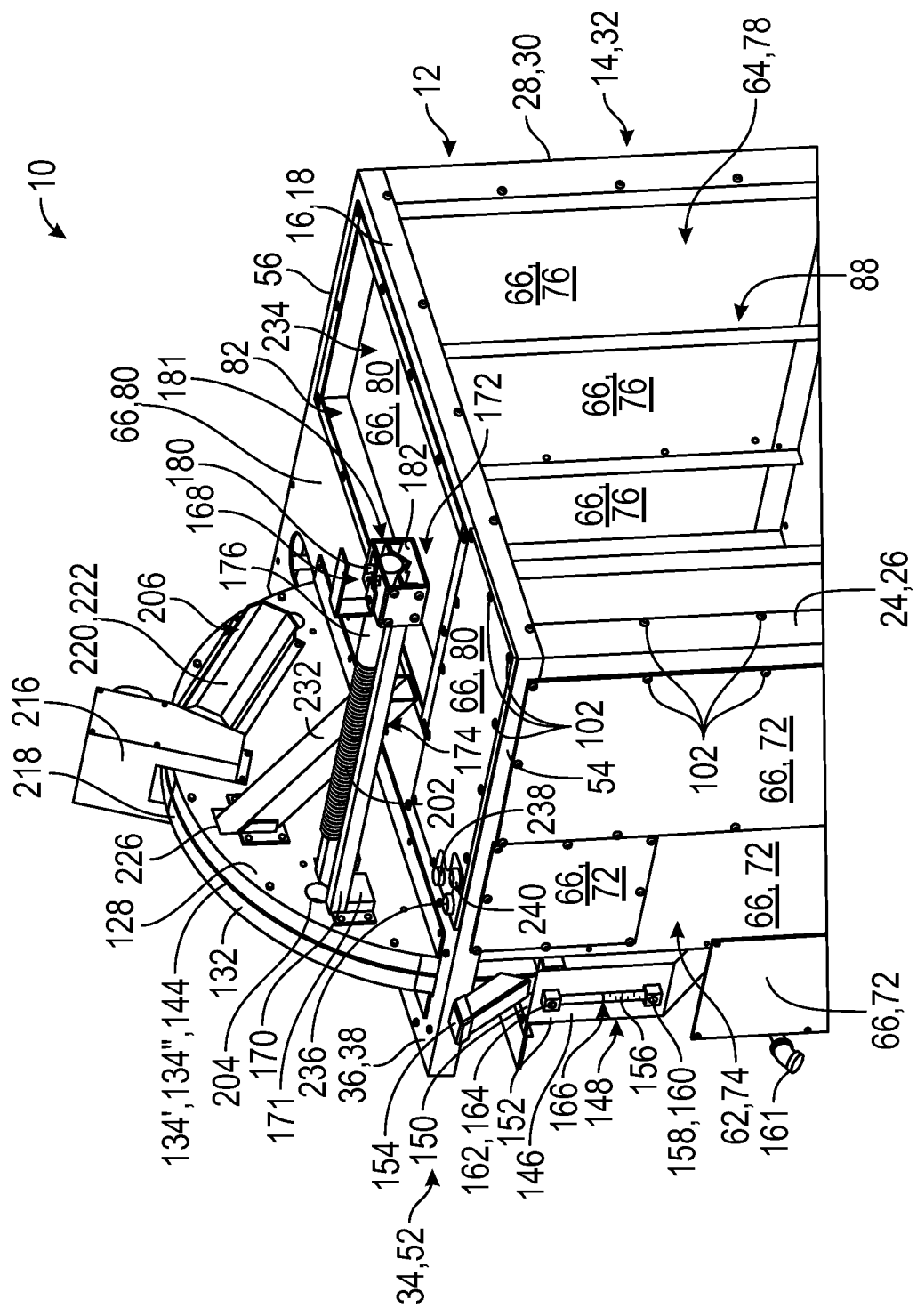
FIG. 5 is an enlarged partial perspective front view of the system and method for cleaning disks of FIG. 2 including a plurality of chips loaded in the loading mechanism according to an exemplary embodiment.

Turning now to FIG. 5, and with continuing reference to FIGS. 1-4, once the locking bar 194 is moved to the unlocked position 198, the horizontal pusher 176 of the feed mechanism 168 is drawn towards distal end 171 of the guide rail 170 from the proximal end 182 by the spring 174. In the example shown in FIG. 5, a stack of chips 202 has been deposited in the v-shaped channel 173 of the guide rail 170. As the horizontal pusher 176 moves towards the distal end 171 of the guide rail 170, a rate of movement of the horizontal pusher 176 is defined by the rotational speed of the cleaning disk 130. That is the chips 202 feed through feed orifice 204 formed in the inner disk housing 128. The feed orifice 204 is sized and shaped to allow the chips 202 to pass freely through the inner disk housing 128 and to be deposited in the holes 142 of the cleaning disk 130. Thus, as each of the holes 142 of the cleaning disk 130 passes by the feed orifice 204, spring tension causes horizontal pusher 176 to move towards the inner disk housing 128 and to push a single chip 202 into a single hole 142 of the cleaning disk 130.

Figure 6:
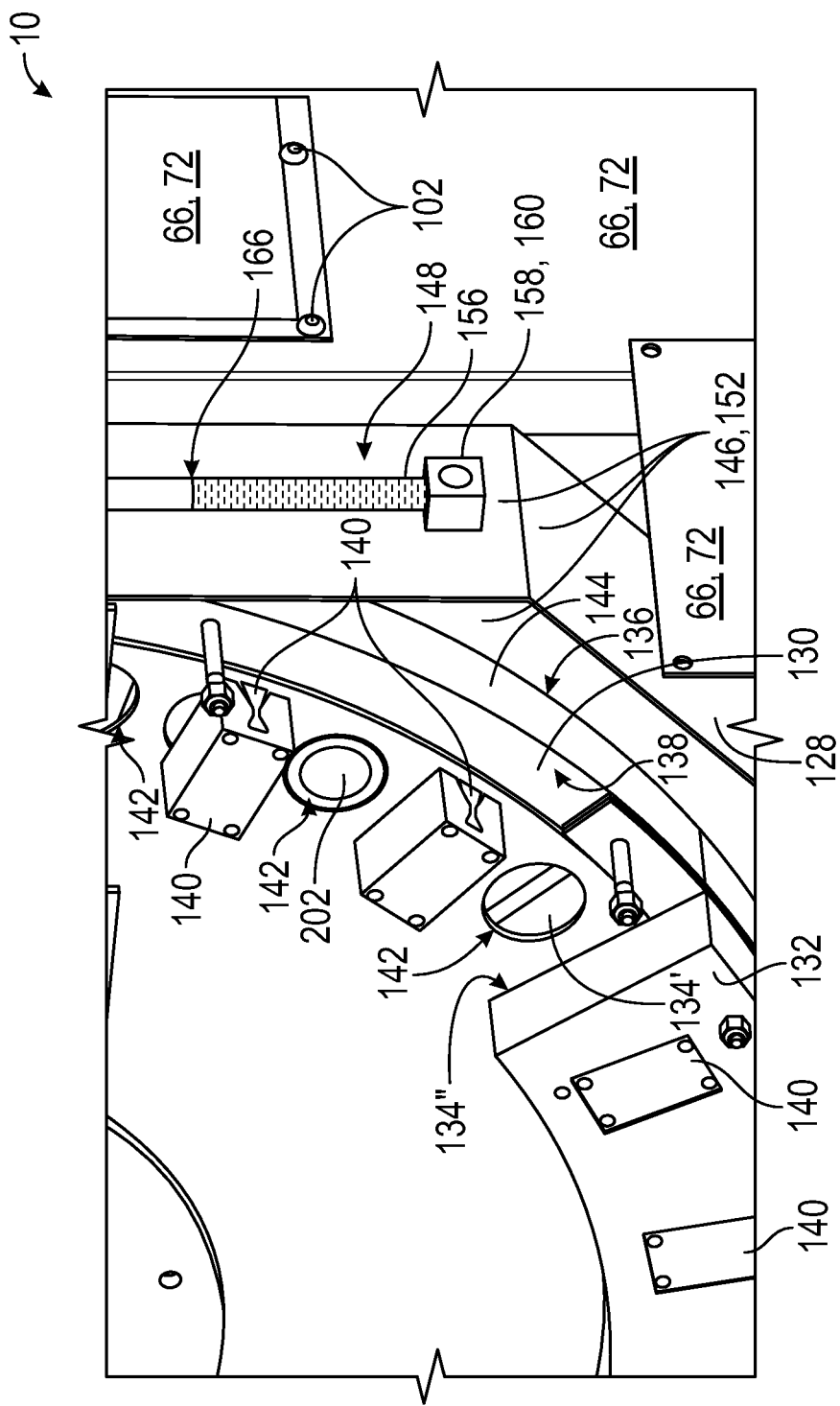
FIG. 6 is an enlarged perspective rear cutaway view of a portion of the system and method for cleaning disks of FIG. 1 showing a cleaning disk and inner and outer disk housings according to an exemplary embodiment.

Turning now to FIG. 6, and with continuing reference to FIGS. 1-5, a partial rear cutaway view of the system 10 is shown in further detail. The outer disk housing 132 is shown in particular. As the cleaning disk 130 rotates, the brushes 140 of each of the inner and outer disk housings 128, 132 contact the chips 202 and agitate the surfaces of the chips 202, thereby removing dirt, grime, biological and non-biological matter, and other surface contamination on the chips 202. In several aspects, the brushes 140 extend laterally towards the cleaning disk 130 and not only contact the inner and outer surfaces 136, 138 of the cleaning disk 130, but actually extend further. That is, the brushes 140 bend against the inner and outer surfaces 136, 138 of the cleaning disk 130 so that as each hole 142 passes one or more of the brushes 140, the brushes 140 extend into the hole 142. Put another way, the distance between a brush 140 on the outer disk housing 132 and the inner disk housing 132 is smaller than a thickness of the cleaning disk 130, and also less than a thickness of the chips 202 to be cleaned.

Figure 7:
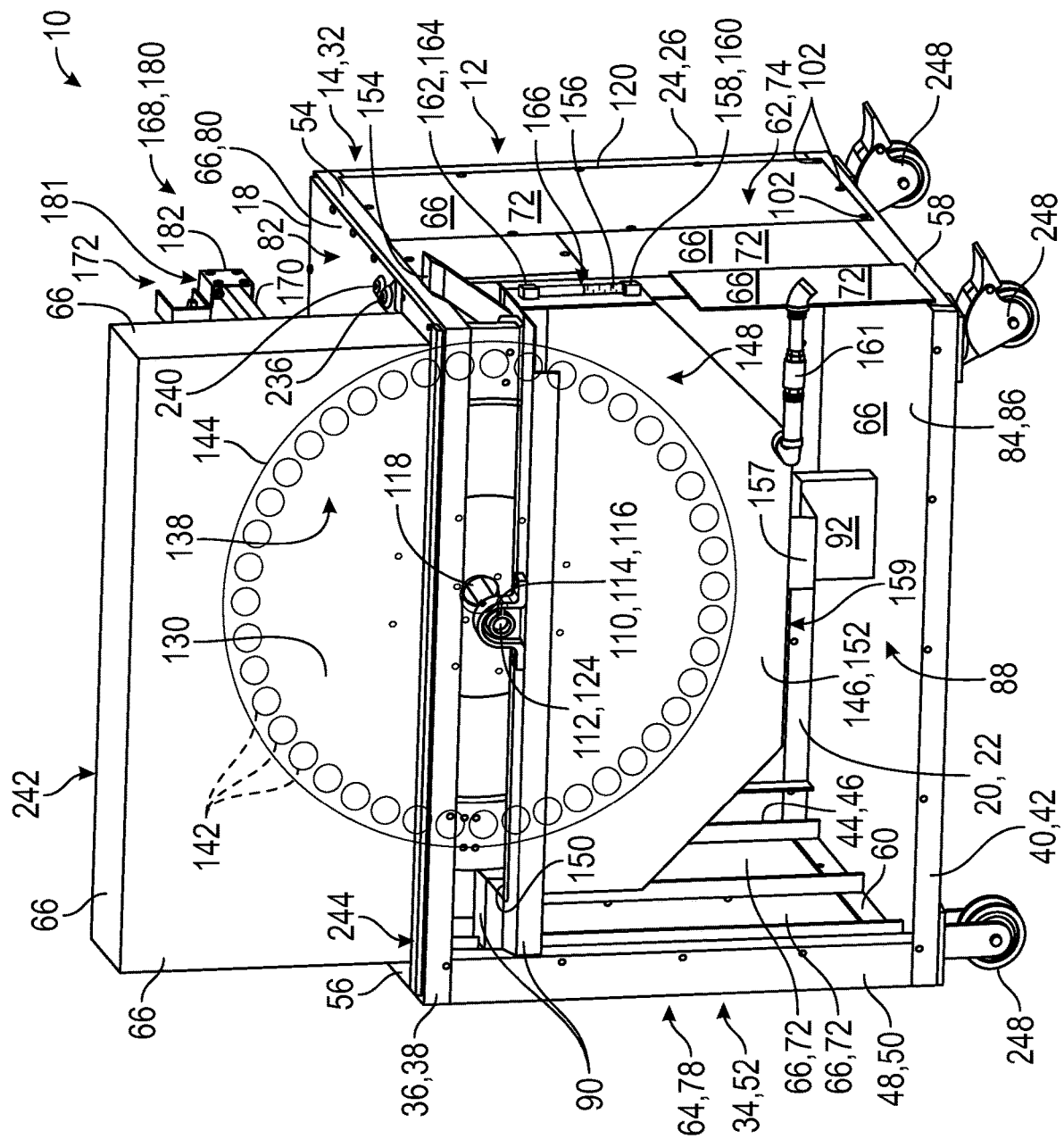
FIG. 7 is a perspective rear view of the system and method for cleaning disks of FIG. 1 in which the front, rear, and a side panel have been removed according to an exemplary embodiment.

Referring now to FIG. 7 and with continuing reference to FIGS. 1-6, once the chips 202 have been loaded into the cleaning disk 130, the cleaning disk 130 carries the chips 202 into the washing tank 146, thereby submerging the chips 202 in the cleaning solution 148. The rotational speed of the cleaning disk 130, the radius "R" of the cleaning disk 130, and the level "L" of the cleaning solution 148 within the washing tank 146 determine an amount of time that the chips 202 are submerged in the cleaning solution 148. The level L of the cleaning solution 148 within the washing tank 146 is always below the support shaft 112 so that the support shaft 112 does not come into contact with the cleaning solution 148. In some examples, the motor 94 drives the driven gear or pulley 110 at approximately 2.5 revolutions per minute. Thus, the cleaning disk 130 makes approximately 2.5 revolutions per minute as well. In an example of a 32-inch diameter cleaning disk 130, at least forty holes 142 are disposed circumferentially around the cleaning disk 130. The holes 142 are spaced apart from one another and do not overlap. Moreover, the holes 142 are disposed at a constant radius from the support shaft 112. In the example, with 40 holes spaced about the perimeter 144 of the cleaning disk 130 as described above, and driven at 2.5 revolutions per minute, a total throughput of at least one hundred chips 202 per minute is possible. It should be appreciated, however, that the dimensions of the cleaning disk 130 can be altered, the number of holes 142 may be altered, and the rotational speed of the cleaning disk 130 may be altered, and that each of these modifications may result in substantial variations in chip 202 throughput of the system 10 without departing from the scope or intent of the present disclosure.

Figure 8:
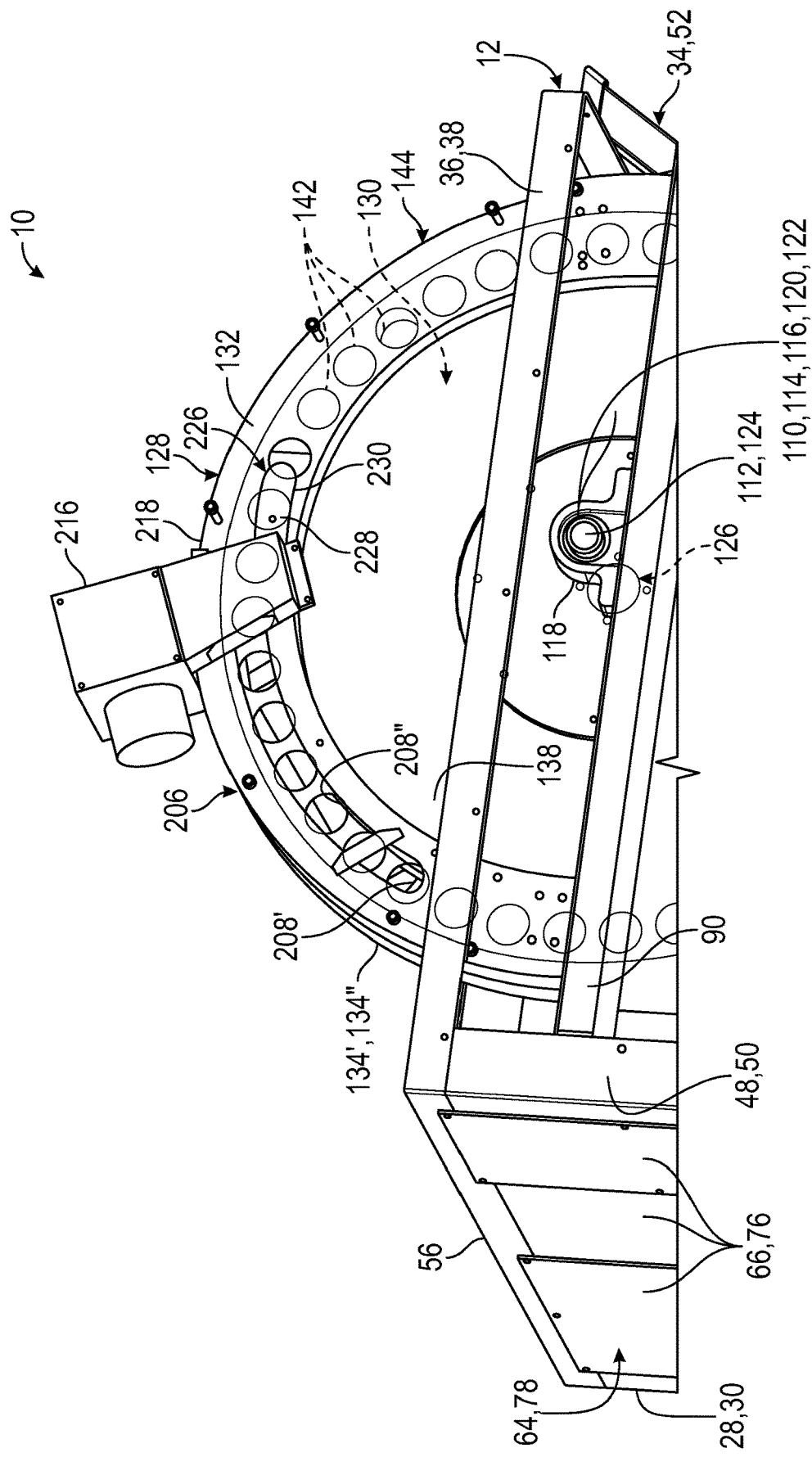
FIG. 8 is a partial perspective rear view of the system and method for cleaning disks of FIG. 1 showing a vent and ejection tab and ejection port according to an exemplary embodiment.

Turning now to FIG. 8, and with continuing reference to FIGS. 1-7, having been loaded into a hole 142 of the cleaning disk 130, passed through the washing tank 146 and the cleaning solution 148, and passing substantially all of the brushes 140, the chip 202 proceeds to a drying area 206 of the system 10. FIG. 8 shows a partial rear cutaway view of the drying area 206 in particular. The drying area 206 consists of two arcuate slots 208', 208", one formed in each of the inner and outer disk housings 128, 132. The arcuate slots 208', 208" extend radially for a distance or width "D" that is less than the diameter of the holes 142 of the cleaning disk 130. The arcuate slots 208', 208" extend circumferentially for approximately one sixth of the More specifically, the arcuate slots 208', 208" extend radially for a width "D" that is smaller than the diameter of any of the chips 202. Because the radial width "D" of the arcuate slots 208', 208" is smaller than the diameter of the chips 202, as the chips 202 move along the arcuate slots 208', 208", the chips 202 are retained within the holes 142, but are also free to rotate within the holes 142.

Figure 9:
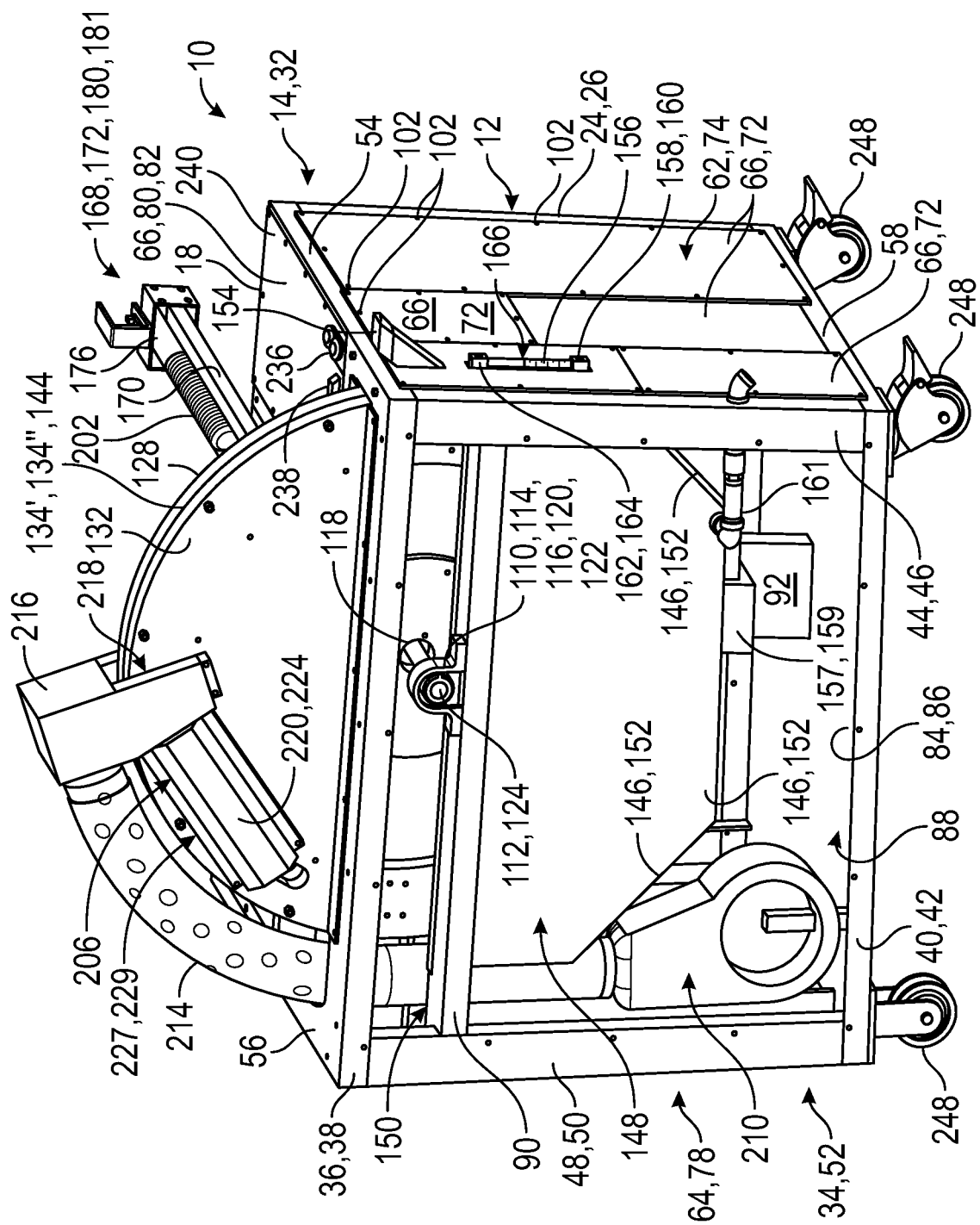
FIG. 9 is a perspective rear view of the system and method for cleaning disks of FIG. 1 in which the front, rear, and a side panel have been removed, and in which a dryer, the vent, and a duct are shown in further detail according to an exemplary embodiment.

Turning now to FIG. 9, and with continuing reference to FIGS. 1-8, a blower 210 is mounted to the structural frame 12. The blower 210 is a motorized device which moves air from one location to another. In effect, the blower 210 may be thought of as a large hair dryer, or another similar apparatus. The blower 210 may be powered by electrical, mechanical, or other means as described hereinabove with respect to the motor 94. In some examples, the motor 94 may also be connected via a serpentine belt (not specifically shown) and one or more pulleys (not specifically show) to the blower 210 and freely rotate a compressor wheel (not shown) within the blower to move air from location to location within the system 10. The blower 210 moves air from an outlet 212 through a duct 214 to a vent 216. The vent 216 is mounted to the inner and outer disk housings 128, 132 proximate to a top 218 of the inner and outer disk housings 128, 132. Air from the vent 216 is forced along the arcuate slots 208', 208" within an air guide 220. The air guide 220 is formed of an inner guide portion 222 and an outer guide portion 224. In one example, the inner and outer guide portions 222, 224 are formed of sheet metal, plastic, nylon, or other materials as described hereinabove and are affixed to the inner and outer disk housings 128, 132 respectively via a plurality of attachment features 102. Having been forced through the inner and outer guide portions 222, 224, air from the blower 210 exits the system 10 via one or more vent holes 225. In some examples, the air is recaptured and recycled by the system 10.

The blower 210 serves an additional function. As well as providing airflow to the air guide 220, the blower 210 includes a heating element 227. In some examples, the heating element 227 may be separate from the blower 210 and attached to or within the duct 214, or attached to or within the air guide 220. The heating element 227 is designed to increase the temperature of air exiting the blower 210 to both decrease chip 202 drying time and decontaminate and disinfect chips 202 as they traverse the air guide 220. In some examples, the heating element 227 is designed to increase a temperature of air in the air guide 220 to between about 120° F. and about 170° F. In another example, the heating element 227 increases the temperature of the air in the air guide 220 to between about 130° F. and about 160° F. In an additional example, the temperature of the air in the air guide 220 is held to about 145° F. to about 155° F., and preferably at least 150° F. It should be appreciated that the ideal temperature of the air in the air guide 220 may vary from application to application, and depends on such factors as rotational speed of the cleaning disk 130, size and length of the arcuate slots 208', 208", size and length of the air guide 220, and the like.

The air guide 220 serves an additional purpose as well. One or more irradiation means are disposed within and supported by the air guide 220. The irradiation means may take any of a variety of forms without departing from the scope or intent of the present disclosure. In some examples, the irradiation means include a plurality of ultraviolet (UV) lamps 229, or the like. More specifically, at least one UV lamp 229 is disposed on and supported by each the inner and outer guide portions 222, 224. In some examples, the UV lamps 229 each have at least a 20 Watt capacity and light from the UV lamps 229 is incident on both sides of each chip 202 for at least fourteen seconds.

Figure 10:
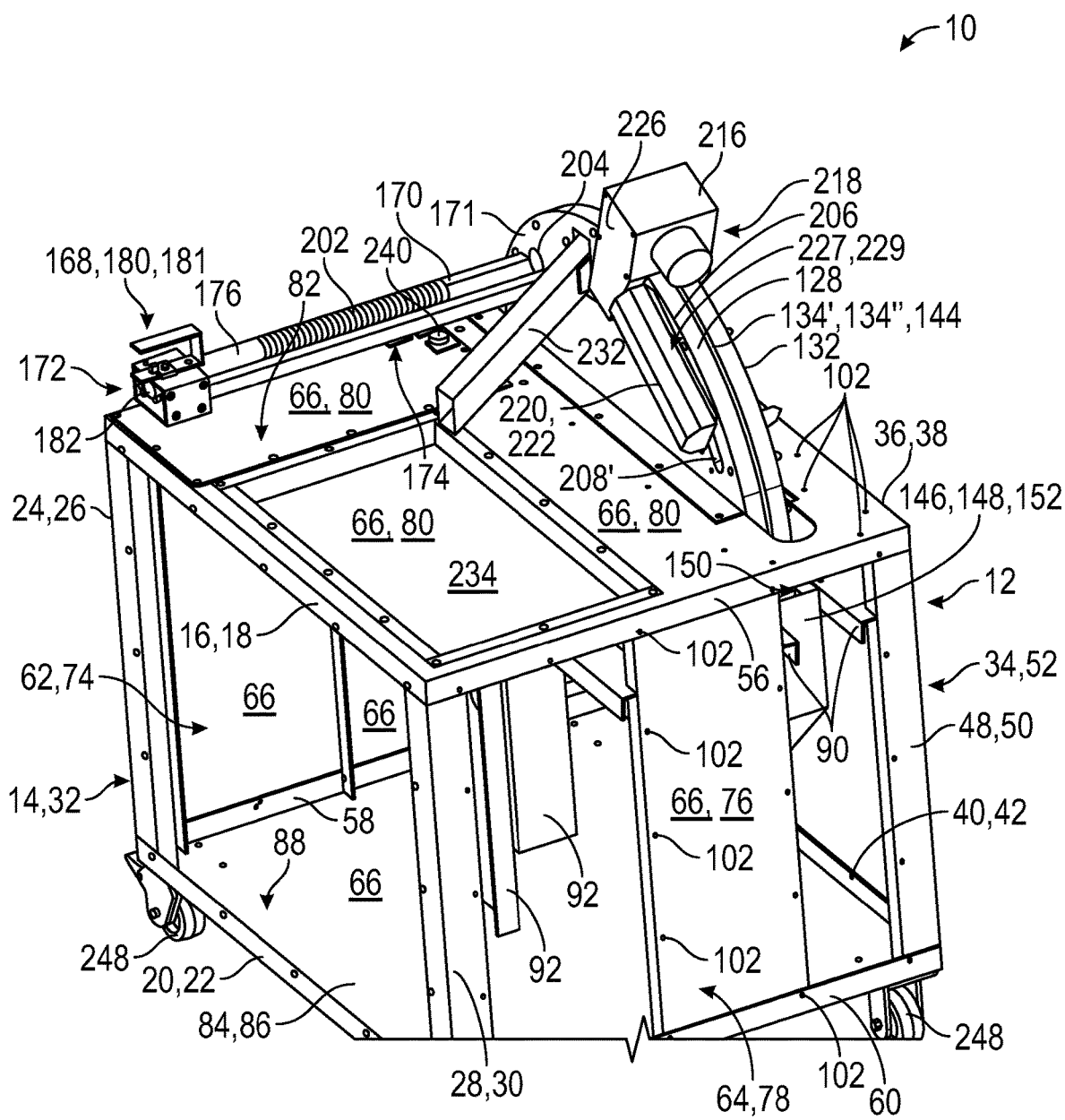
FIG. 10 is a perspective side view of the system and method for cleaning disks of FIG. 1 in which the front, rear, and some side panels have been removed, and in which the disk loading mechanism and a chute are shown in further detail according to an exemplary embodiment.

Turning now to FIG. 10, and with continuing reference to FIGS. 1-9, once the chips 202 have been loaded into the cleaning disk 130, submerged in the cleaning solution 148 within the washing tank 146, dried and irradiated by heated air and UV lamps 229 for at least fourteen seconds in the air guide 220, the chips 202 arrive at a chip ejection port 226. The chip ejection port 226 is an orifice formed in the inner disk housing 128 and sized to allow unhindered movement of the chips 202. An ejection tab or finger 228 is disposed opposite the chip ejection port 226 on the outer disk housing 132. The ejection tab 228 is a lever-arm or spring that protrudes through an ejector aperture 230 formed in the outer disk housing 132 and towards the inner disk housing 128. The ejection tab 228 may be formed of any of a variety of known materials, such as metals, metal alloys, ceramics, nylons, plastics, PTFEs, UHMWs, composite materials, rubbers and rubber compounds, or the like. When one of the holes 142 is aligned with both the chip ejection port 226 and the ejector aperture 230, the ejection tab 228 extends entirely through the hole 142 and in some examples, may even extend partially through the chip ejection port 226 of the inner disk housing 128. Thus, as the cleaning disk 130 rotates and chips 202 are brought to the ejection port 226, the ejection tab 228 pushes the chips 202 out of the holes 142 and through the chip ejection port 226 to a chute 232.

The chute 232 is formed of any of a variety of known materials, such as metals, metal alloys, ceramics, nylons, plastics, PTFEs, UHMWs, composite materials, rubbers and rubber compounds, or the like. The chute 232 is sloped downward relative to the top 218 of the inner and outer disk housings 128, 132, and channels chips to a sorting tray 234 mounted to or formed as a portion of the top surface 82 of the system 10. In some examples, the sorting tray 234 may be lined with a padded material that is optimized to reduce the potential for damage to the chips 202 or other objects to be cleaned as the chips 202 or other objects drop through the chute 232 into the sorting tray 234. Additional absorbent drying materials may also be used as a lining material for the sorting tray 234.

A start button 236 and a stop button 238 are disposed on at least one of the panels 66 of the system 10. In the examples shown in FIGS. 1-3, 5, 7, 9, and 10 the start and stop buttons 236, 238 are disposed on one of the panels 66 forming a portion of the top surface 82 of the system 10. The start button 236 communicates with the motor 94 and engages the motor 94 to drive the cleaning disk 130. The stop button 238 communicates with the motor 94 and disengages the motor 94 to cause the cleaning disk 130 to stop rotating. In some examples, the start and stop buttons 236, 238 may be a rocker switch, a slider engaging variable motor 94 speeds such as a rheostat switch, or the like.

An indicator 240 is disposed on at least one of the panels 66, and preferably one of the panels 66 forming a portion of the top surface 82 of the system as well 10. The indicator 240 provides feedback to a system user or operator regarding the status of the system 10. In one aspect, the indicator 240 provides visual and/or audible feedback to the user regarding a quality of the cleaning solution 148 within the washing tank 146. The indicator 240 may be passive or active. In an example of a passive indicator 240, the indicator 240 is a manually reset timer. When new cleaning solution 148 is added to the washing tank 146 the indicator 240 may be reset. After a predetermined quantity of time in use after the reset, the indicator 240 provides audio and/or visual feedback to an operator indicating that the cleaning solution 148 has aged a predetermined amount and is due for replacement.

In an example of an active indicator 240, the indicator 240 is connected to a sensor (not specifically shown) disposed in or on the washing tank 146. The sensor may be an optical or chemical sensor, or the like and is disposed on or within the washing tank 146. When the sensor detects a change in optical, chemical, or other such quality of the cleaning solution 148 that causes the cleaning solution 148 to fall below a predetermined optical, chemical, or other such quality threshold, the sensor sends a signal to the indicator 240 and the indicator 240 provides audio and/or visual feedback to the operator indicating that the cleaning solution 148 is due for replacement. More specifically, if the sensor determines that the cleaning solution 148 is dirty, no longer chemically or biologically effective, or the like, then the cleaning solution 148 can be drained via the drain plug or pipe 161. The cleaning solution 148 may be drained by manual or automatic processes. New cleaning solution 148 is then added via the filler neck 154. More specifically, the new cleaning solution 148 can be added manually, or via a remote reservoir (not shown) that may be automatically emptied into the washing tank 146 once the tank has been emptied. It should be appreciated that the particular orientation of the start and stop buttons 236, 238 and the indicator 240 may vary from application to application without departing from the scope or intent of the present disclosure. Moreover, the start and stop buttons 236, 238, and indicator 240 may be located on entirely different panels or in entirely different orientations on the system 10.

A top housing 242 formed from one or more enclosing panels 66 encloses and surrounds the inner and outer disk housings 128, 132, and the cleaning disk 130. In several aspects, the top housing is a substantially rectangular prism-shaped container with an open side 244 facing downwards. The open side 244 allows the top housing 242 to fit over and enclose the inner and outer disk housings 128, 132, and the cleaning disk 130. A plurality of apertures, holes, or slots 246 are formed through the top housing 242. The apertures, holes, or slots 246 are sized, shaped, and located to fit around, but not impede the feed mechanism 168 and the chute 232. The top housing 242 of some examples is freely movable and merely rests on top of the top surface 82 of the system 10. In other examples, the top housing 242 is attached to the structural frame 12 and/or the top surface 82, or other panels 66 of the system 10 via one or more attachment features 102 as described hereinabove.

The system 10 is also optimized for portability. Specifically, a plurality of casters 248, sliders, or the like are mounted to the structural frame 12 or the bottom surface 86 of the system 10. The casters 248 may be any known variety of caster, wheel, slider, or the like. The casters 248 provide mobility to the system 10 such that an operator can push the system 10 on flat or inclined surfaces from location to location. For example, an operator can push the system 10 from one gaming table to another, or from one location within a casino to another utilizing the casters 248. In some examples, the casters 248 are lockable, thereby providing locational stability to the system 10 while the system 10 is in use. The system 10 is also portable in that the system 10 can easily be hydraulically and/or electrically connected to ambient sources of hydraulic, pneumatic, and/or electrical input. In several aspects, the motor 94, blower 210, and the system 10, more generally are adapted to accept and be powered by standardized electrical energy provisions, such as wall outlets (not specifically shown) having alternating current (AC) at 115 Volts on a twenty amp breaker at 50-60 Hz. In another example, the system 10 may be adapted to be used in other countries or on differing sources of electrical energy, such as 240-Volt AC sources, or in foreign countries using alternate power sources. Some examples of the system 10 may even run on direct current (DC) or a combination of AC and DC power supplies so that the system 10 can be powered by a portable power supply, such as a battery or a portable generator (not shown). Likewise, in some examples, the system 10 may dilute the cleaning solution 148 with water provided by household or building plumbing features and a hose (not shown). However, it should be appreciated that variations in electrical power supply type and format, and/or plumbing are intended to be within the spirit and scope of the present disclosure.

Figure 11:
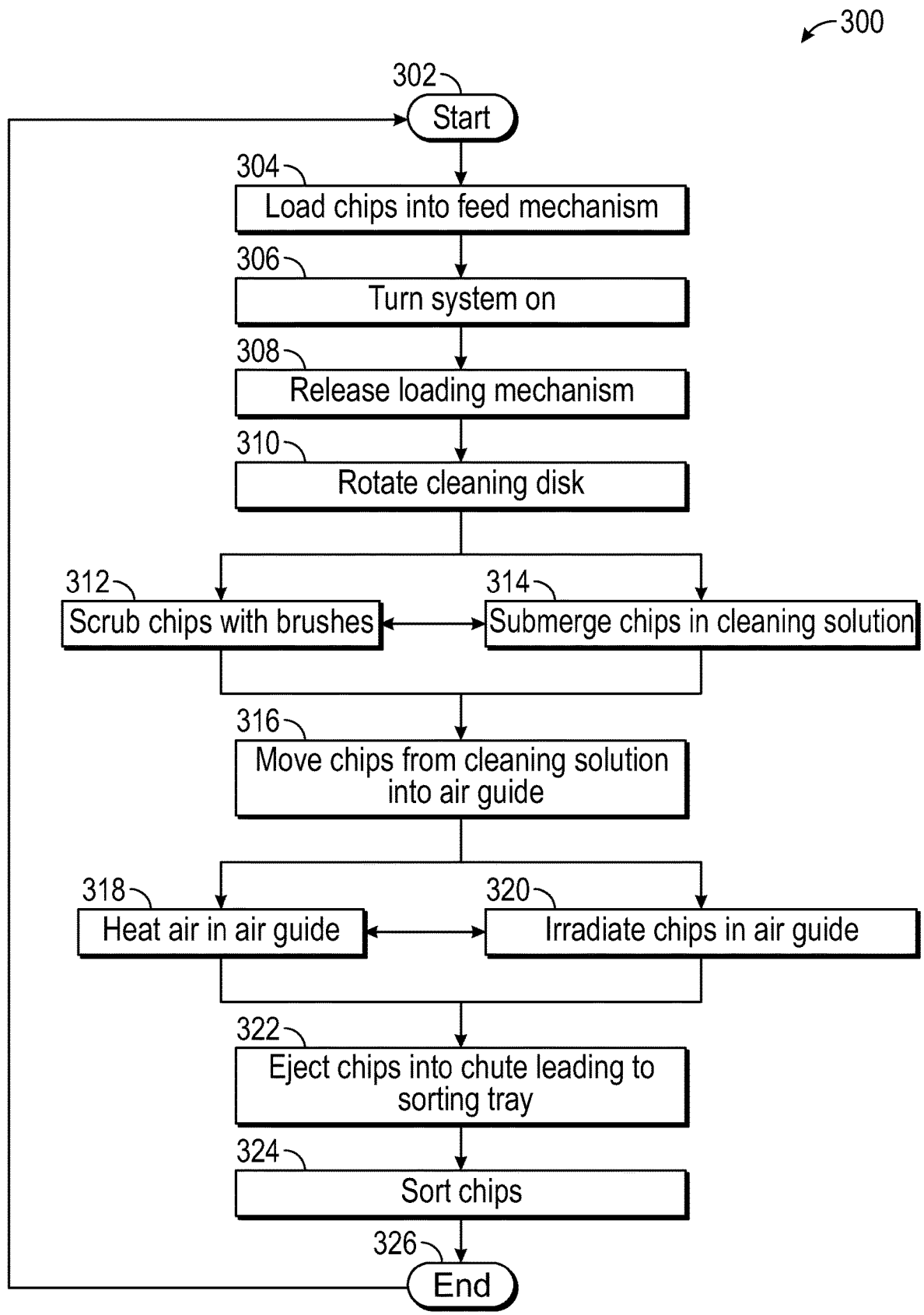
FIG. 11 is a flowchart depicting the method for cleaning disks of FIG. 1 according to an exemplary embodiment.

Turning now to FIG. 11, a method 300 of cleaning disks using the system 10 of the present disclosure begins at block 302. At block 304, a system 10 user loads objects to be cleaned, such as chips 202, into the v-shaped channel 173. To do so, the system 10 user retracts the trolley 172 as far from the cleaning disk 130 as possible along the v-shaped channel 173. The system 10 user then places a one or more chips 202 into the v-shaped channel 173 between the horizontal pusher 176 and the cleaning disk 130. At block 306, the system 10 user engages the system 10 by enabling power or otherwise turning on or powering up the system 10. At block 308, the system 10 user releases the spring-loaded release mechanism 180 thereby selectively unlocking the trolley 172 from the locked position 181 at a proximal end 182 of the guide rail 170. The spring 174 biasing the trolley 172 towards the cleaning disk 130 then progressively cause the chips 202 to be moved along the guide rail 170 and into the plurality of circumferentially-arranged holes 142 spaced around the perimeter 144 of the cleaning disk 130. At block 310, the cleaning disk 130 is rotated by the motor 94 and carries the chips 202 into the washing tank 146. The cleaning disk 130 rotates at a rate which ensures that each of the chips 202 is held within the cleaning solution 148 for a predetermined amount of time optimized to sanitize and disinfect the chips 202. At block 312, as the cleaning disk 130 rotates the plurality of brushes 140 contacts and scrubs or otherwise agitates the surfaces of the chips 202. At block 314, the chips 202 are submerged in the cleaning solution 148 in the washing tank 146 for a predetermined period of time optimized to clean and otherwise disinfect the surfaces of the chips 202. It should be appreciated that the surface agitation occurring at block 312 and the submergence in cleaning solution 148 of block 314 may occur simultaneously, sequentially, or partially simultaneously and partially sequentially without departing from the scope and intent of the present disclosure. That is some of the brushes 140 may be disposed above the cleaning solution 148 and "dry-scrub" the chips 202, while some of the brushes 140 may be submerged within the cleaning solution 148 simultaneously agitating the surfaces of the chips 202 while also applying the cleaning solution 148 to the surfaces in a "wet scrub" process.

At block 316 the chips 202 are carried up and out of the cleaning solution 148 by the cleaning disk 130 and into the air guide 220. The blower 210 forces air through the air guide 220 and over the surfaces of the chips 202, thereby removing substantially all of the cleaning solution 148 which might have clung to the surfaces of the chips 202. At block 318, which occurs simultaneously with block 316, the heating element 227 increases a temperature of the air blown through the air guide 220 to between about 120° F. and about 170° F. In another example, the heating element 227 increases the temperature of the air in the air guide 220 to between about 130° F. and about 160° F. In an additional example, the temperature of the air in the air guide 220 is held to about 145° F. to about 155° F., and preferably at least 150° F. At block 320, which also occurs simultaneously with blocks 316 and 318, the UV lamp or lamps 229 irradiate the surfaces of the chips 202 with ultraviolet light. Each of the UV lamps 229 having at least a 20 Watt capacity and ultraviolet light from the UV lamps 229 is incident on both sides of each chip 202 for at least fourteen seconds.

The method 300 then proceeds to block 322 where the chips 202 are ejected from the cleaning disk 130 by an ejection tab 228 and through the chip ejection port 226 and into the chute 232 into the sorting tray 234. Absorbent drying materials may also be used as a lining material for the sorting tray 234. At block 324, the system 10 user sorts the chips 202. At block 326, the method 300 ends and returns to block 302 where the system 10 user loads additional chips 202 or other such objects to be cleaned into the v-shaped channel 173 of the system 10 to begin the cleaning process again. The system 10 including the motor 94 may run continuously while on or otherwise engaged, or may include sensors or the like which disengage operation of the motor 94 when certain conditions are met. For example, the system 10 may be in an "on" state, but if no objects to be cleaned are present within the system 10, the motor 94 may disengage to reduce power consumption, cleaning solution 148 evaporation or other such waste, and the like.

While in the foregoing description, the system 10 of the present disclosure has been described has including a single cleaning disk 130 supported between inner and outer disk housings 128, 132, a single washing tank 146, and the like, it should be appreciated that this description is not intended to be so limiting. In some examples, the system 10 of the present disclosure is replicated such that multiple parallel cleaning disks 130 may be used. In one particular example, substantially the entire system 10 as described hereinabove is replicated in a mirrored position. A single motor 94 may drive multiple cleaning disks 130, or multiple motors 94 may be used.

A system and method for cleaning disks of the present disclosure offers several advantages. These include high throughput, plug-and-play usability and portability, and the ability to operate continuously and substantially without the need for human intervention in the cleaning process.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. A system for cleaning disks comprises:
a rotatable cleaning disk rotatably supported by a structural frame, the rotatable cleaning disk defining a plurality of holes, the plurality of holes carrying disks to be cleaned, the rotatable cleaning disk disposed between a first plurality of brushes and a second plurality of brushes, the first plurality of brushes facing the second plurality of brushes, each of the first plurality of brushes and the second plurality of brushes contacting and agitating surfaces of the disks;
a washing tank supported by the structural frame and defining a reservoir of cleaning solution, at least a portion of the rotatable cleaning disk is submerged in the cleaning solution in the washing tank;
one or more enclosing panels extending across and affixed to the structural frame, the one or more enclosing panels defining an enclosure within the structural frame;
a motor disposed within the enclosure and mounted to the structural frame, the motor having a shaft extending from a first end proximate the motor to a second end distal to the motor;
a drive gear or pulley mounted to and fixed for common rotation with the shaft of the motor proximate the second end of the shaft; and
a driven gear or pulley mounted to and fixed for common rotation with a first end of a support shaft, the support shaft rotatably mounted to the structural frame between the first end of the support shaft and a second end of the support shaft, the rotatable cleaning disk mounted to and fixed for common rotation with the second end of the support shaft, the drive gear rotatably connected to the driven gear by a continuous drive belt,
an inner disk housing supported by the structural frame, the first plurality of brushes mounted to the inner disk housing;
an outer disk housing parallel to the inner disk housing, the outer disk housing supported by the structural frame, the second plurality of brushes mounted to the outer disk housing; and
wherein the cleaning disk is disposed between the inner disk housing and the outer disk housing, wherein the first and second pluralities of brushes are separated by a distance less than a thickness of the cleaning disk and less than a thickness of the disks to be cleaned such that the first plurality of brushes contacts an inner surface of the cleaning disk and the second plurality of brushes contacts an outer surface of the cleaning disk; the cleaning disk rotatably supported by the structural frame and rotated by the motor.

2. The system of claim 1 further comprising:
a plurality of holes formed through the cleaning disk, the holes disposed circumferentially around the cleaning disk and spaced apart from one another, the cleaning disk rotating at a predetermined rotational speed and positioned so that each of the plurality of holes is directly adjacent a feed mechanism at a single point in the rotation of the cleaning disk.

3. The system of claim 2 wherein the feed mechanism is supported by the structural frame and automatically feeds disks to be cleaned into the system.

4. The system of claim 1 wherein at least some of the first and second pluralities of brushes are submerged in the cleaning solution, the first and second pluralities of brushes agitating surfaces of the disks to be cleaned.

5. The system of claim 1 further comprising:
an ejection port formed through the inner disk housing and sized to allow passage of cleaned disks;
an ejection tab located at the ejection port and directing the cleaned disks through the ejection port and into a chute, the cleaned disks passing down the chute; and
a sorting tray disposed at an end of the chute opposite the ejection tab and receiving the cleaned disks from the chute.

6. A method for cleaning disks comprising:
placing disks to be cleaned into a disk cleaning system, the disk cleaning system having a structural frame, a rotatable cleaning disk rotatably mounted to the structural frame and disposed between a first plurality of brushes and a second plurality of brushes, the first plurality of brushes directly across from and facing the second plurality of brushes; an inner disk housing supported by the structural frame, the first plurality of brushes mounted to the inner disk housing; an outer disk housing parallel to the inner disk housing, the outer disk housing supported by the structural frame, the second plurality of brushes mounted to the outer disk housing; and wherein the cleaning disk is disposed between the inner disk housing and the outer disk housing, wherein the first and second pluralities of brushes are separated by a distance less than a thickness of the cleaning disk and less than a thickness of the disks to be cleaned such that the first plurality of brushes contacts an inner surface of the cleaning disk and the second plurality of brushes contacts an outer surface of the cleaning disk; the cleaning disk rotatably supported by the structural frame and rotated by a motor;

contacting and agitating surfaces of the disks to be cleaned with the first plurality of brushes and the second plurality of brushes;

rotating the rotatable cleaning disk at a predetermined rate;

submerging a portion of the rotatable cleaning disk, carrying the disks to be cleaned, in a washing tank for a predetermined quantity of time, the washing tank mounted to the structural frame and defining a reservoir filled with a cleaning solution;

ejecting cleaned disks from the disk cleaning system into a sorting tray.

7. The method of claim 6 wherein placing disks to be cleaned into a cleaning system further comprises:

loading the disks to be cleaned into a feed mechanism supported by the structural frame and automatically feeding disks to be cleaned into the system, wherein a plurality of holes is formed through the cleaning disk, the holes are disposed circumferentially around the cleaning disk and spaced apart from one another, the cleaning disk rotates at a predetermined rotational speed and is positioned so that each of the plurality of holes is directly adjacent the feed mechanism at a single point in the rotation of the cleaning disk.

8. The method of claim 6 wherein agitating surfaces of the disks to be cleaned further comprises:

passing the disks to be cleaned between the first plurality of brushes and the second plurality of brushes, wherein the first plurality of brushes and the second plurality of brushes are separated by a distance less than a thickness of the cleaning disk and less than a thickness of the disks to be cleaned.

9. The method of claim 6 wherein rotating the rotatable cleaning disk at a predetermined rate further comprises:

utilizing the motor mounted to the structural frame to rotate the cleaning disk via a drive gear or pulley mounted to and fixed for common rotation with a shaft of the motor and rotatably connected by a continuous drive belt to a driven gear or pulley, the driven gear or pulley mounted to and fixed for common rotation with a first end of a support shaft, the support shaft rotatably mounted to the structural frame between the first end of the support shaft and a second end of the support shaft, the rotatable cleaning disk mounted to and fixed for common rotation with the second end of the support shaft, wherein the motor through the continuous drive belt and the drive gear or pulley and the driven gear or pulley causes the rotatable cleaning disk to rotate at approximately 2.5 revolutions per minute.

10. A system for cleaning disks comprising:

a structural frame;

one or more enclosing panels extending across and affixed to the structural frame, the enclosing panels further defining an enclosure;

a feed mechanism supported by the structural frame and automatically feeding disks to be cleaned into the system;

an inner disk housing supported by the structural frame and having a first plurality of brushes;

an outer disk housing parallel to the inner disk housing, the outer disk housing supported by the structural frame and having a second plurality of brushes placed directly opposite the first plurality of brushes so that the first plurality of brushes faces the second plurality of brushes;

a cleaning disk disposed between the inner disk housing and the outer disk housing such that the first plurality of brushes contacts an inner surface of the cleaning disk and the second plurality of brushes contacts an outer surface of the cleaning disk; the cleaning disk rotatably supported by the structural frame and rotated by a motor;

the motor disposed within the enclosure and mounted to the structural frame, the motor having a shaft;

a drive gear or pulley mounted to and fixed for common rotation with the shaft of the motor;

a driven gear or pulley mounted to and fixed for common rotation with a first end of a support shaft, the support shaft mounted to the structural frame between the first end of the support shaft and a second end of the support shaft, the cleaning disk mounted to and fixed for common rotation with the second end of the support shaft, the drive gear rotatably connected to the driven gear by a continuous drive belt;

a plurality of holes formed through the cleaning disk, the holes disposed circumferentially around the cleaning disk and spaced apart from one another, the cleaning disk rotating at a predetermined rotational speed and positioned so that each of the plurality of holes is directly adjacent the feed mechanism at a single point in the rotation of the cleaning disk;

a washing tank supported by the structural frame and defining a reservoir of cleaning solution, the cleaning disk positioned so that a portion of the cleaning disk is submerged into the cleaning solution, at least some of the first and second pluralities of brushes being submerged in the cleaning solution, the first and second pluralities of brushes separated by a distance less than a thickness of the cleaning disk and less than a thickness of the disks to be cleaned, the first and second pluralities of brushes agitating surfaces of the disks to be cleaned;

an ejection port formed through the inner disk housing and sized to allow passage of disks which have now been cleaned;

an ejection tab located at the ejection port and forcing cleaned disks through the ejection port and into a chute, cleaned disks passing down the chute; and a sorting tray disposed at an end of the chute opposite the ejection tab and receiving cleaned disks from the chute.

* * * * *